(12) United States Patent
Lukin et al.

(10) Patent No.: US 11,596,408 B2
(45) Date of Patent: *Mar. 7, 2023

(54) MAGNETIC ANASTOMOSIS DEVICES AND METHODS OF DELIVERY

(71) Applicant: G.I. Windows, Inc., Westwood, MA (US)

(72) Inventors: Peter Lukin, Norfolk, MA (US); Robert F. Beisel, Robesonia, PA (US); Christopher Thompson, Needham, MA (US); Marvin Ryou, Melrose, MA (US); James Wright, Westwood, MA (US)

(73) Assignee: G.I. Windows, Inc., Westwood, MA (US)

( * ) Notice: Subject to any disclaimer, the term of this patent is extended or adjusted under 35 U.S.C. 154(b) by 283 days.

This patent is subject to a terminal disclaimer.

(21) Appl. No.: 17/158,542

(22) Filed: Jan. 26, 2021

(65) Prior Publication Data

US 2021/0244414 A1 Aug. 12, 2021

Related U.S. Application Data

(63) Continuation of application No. 15/988,577, filed on May 24, 2018, now Pat. No. 10,932,780, which is a
(Continued)

(51) Int. Cl.
*A61F 2/856* (2013.01)
*A61M 27/00* (2006.01)
(Continued)

(52) U.S. Cl.
CPC .......... *A61B 17/11* (2013.01); *A61B 17/1114* (2013.01); *A61B 2017/00004* (2013.01); *A61B 2017/0034* (2013.01); *A61B 2017/00309* (2013.01); *A61B 2017/00323* (2013.01); *A61B 2017/00876* (2013.01); *A61B 2017/1107* (2013.01); *A61B 2017/1117* (2013.01); *A61B 2017/1132* (2013.01); *A61B 2017/1139* (2013.01)

(58) Field of Classification Search
CPC ................. A61B 17/11; A61B 17/1114; A61B 2017/1132; A61B 2017/1139; A61B 2017/0034; A61B 2017/00876
See application file for complete search history.

(56) References Cited

U.S. PATENT DOCUMENTS

2005/0283235 A1* 12/2005 Kugler .................. A61F 5/0069
600/30
2009/0125042 A1* 5/2009 Mouw ................. A61B 17/1114
606/153
(Continued)

*Primary Examiner* — Anh T Dang
(74) *Attorney, Agent, or Firm* — Nutter McClennen & Fish LLP

(57) ABSTRACT

The invention concerns delivering paired magnetic anastomosis devices to either side of tissues to be joined. The magnetic anastomosis devices are coupled to a guide element that facilitates delivery and manipulation of the devices when using minimally-invasive techniques such as endoscopy and laparoscopy. Elongated manipulators and guide tubes ae also disclosed that improve a user's dexterity with the devices during placement.

15 Claims, 27 Drawing Sheets

Related U.S. Application Data continuation of application No. 14/805,916, filed on Jul. 22, 2015, now Pat. No. 10,182,821.

(60) Provisional application No. 62/158,981, filed on May 8, 2015, provisional application No. 62/028,196, filed on Jul. 23, 2014.

(51) Int. Cl.
*A61M 39/22* (2006.01)
*A61B 17/11* (2006.01)
*A61B 17/00* (2006.01)

(56) References Cited

U.S. PATENT DOCUMENTS

| | | | |
|---|---|---|---|
| 2011/0098731 A1* | 4/2011 | Whitbrook | A61F 2/0018 606/151 |
| 2015/0164508 A1* | 6/2015 | Hernandez | A61B 17/1114 606/153 |

* cited by examiner

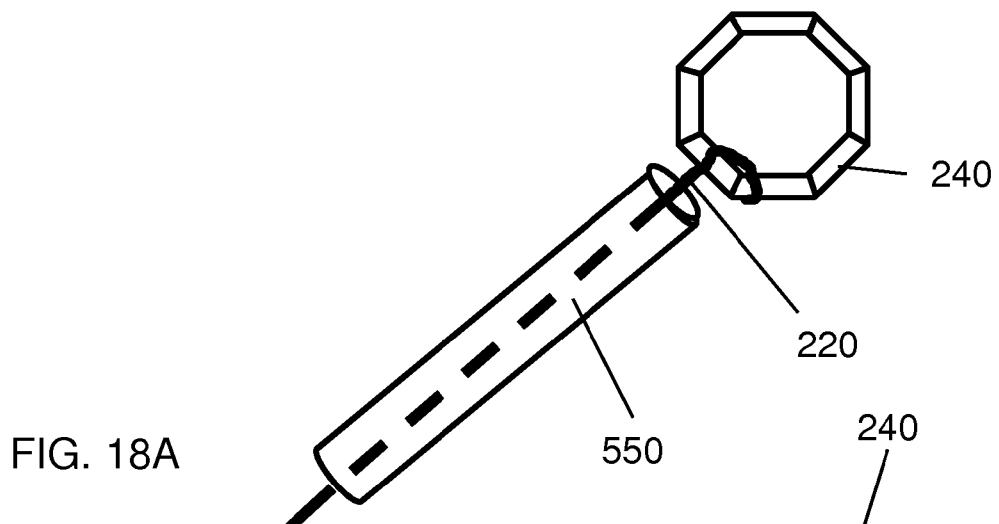
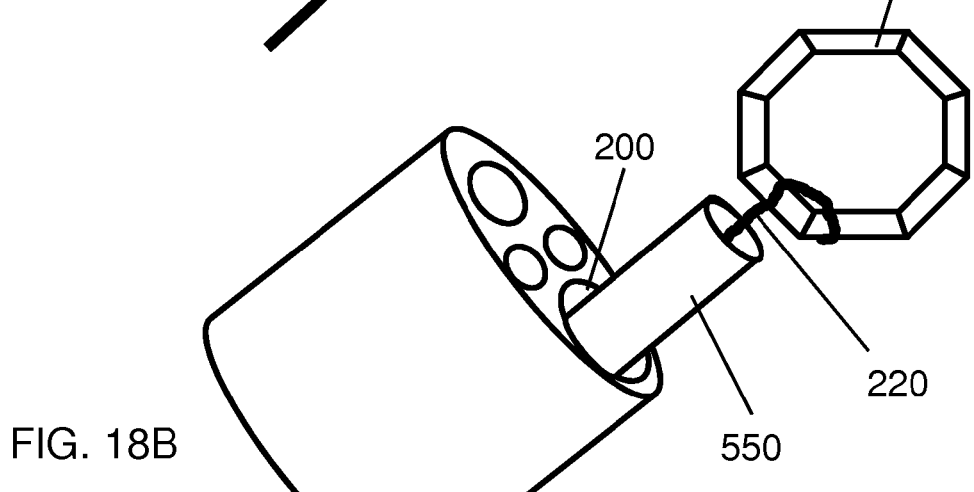
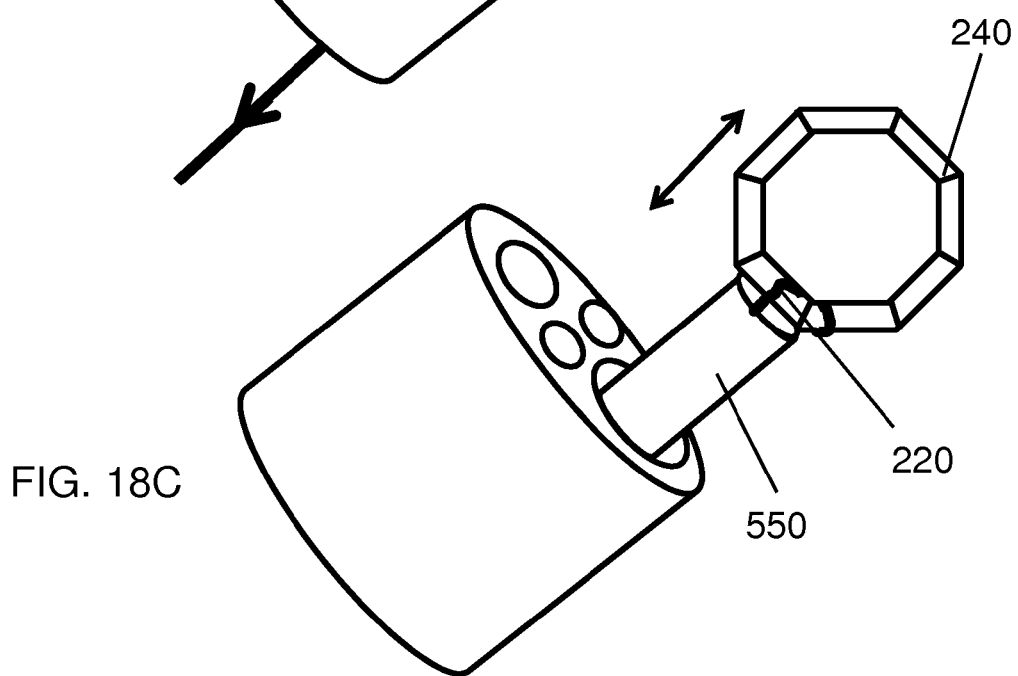

MAGNETIC ANASTOMOSIS DEVICES AND METHODS OF DELIVERY

CROSS-REFERENCE TO RELATED APPLICATIONS

This application is a continuation of U.S. patent application Ser. No. 15/988,577, filed May 24, 2018, which is a continuation of U.S. patent application Ser. No. 14/805,916, filed Jul. 22, 2015 (now U.S. Pat. No. 10,182,821), which claims the benefit of, and priority to, U.S. Provisional Application Ser. No. 62/028,196, filed Jul. 23, 2014, and U.S. Provisional Application Ser. No. 62/158,981, filed May 8, 2015, the contents of each of which are incorporated by reference herein in their entirety.

FIELD OF THE INVENTION

The invention relates to deployable magnetic compression devices and their use for creating anastomoses, e.g., in the gastrointestinal tract. The devices are especially suitable for minimally-invasive delivery, e.g., using endoscopic and/or laparoscopic techniques.

BACKGROUND

Bypasses of the gastroenterological (GI), cardiovascular, or urological systems are typically formed by cutting holes in tissues at two locations and joining the holes with sutures or staples. A bypass is typically placed to route fluids (e.g., blood, nutrients) between healthier portions of the system, while bypassing diseases or malfunctioning tissues. The procedure is typically invasive, and subjects a patient to risks such as bleeding, infection, pain, and adverse reaction to anesthesia. Additionally, a bypass created with sutures or staples can be complicated by post-operative leaks and adhesions. Leaks may result in infection or sepsis, while adhesions can result in complications such as bowel strangulation and obstruction. While traditional bypass procedures can be completed with an endoscope, laparoscope, or robot, it can be time consuming to join the holes in the tissues. Furthermore, such procedures require specialized expertise and equipment that is not available at many surgical facilities.

As an alternative to sutures or staples, surgeons can use mechanical couplings or magnets to create a compressive anastomosis between tissues. For example, compressive couplings or paired magnets can be delivered to tissues to be joined. Because of the strong compression, the tissue trapped between the couplings or magnets is cut off from its blood supply. Under these conditions, the tissue becomes necrotic and degenerates, and at the same time, new tissue grows around points of compression, i.e., on the edges of the coupling. When the coupling is removed, a healed anastomosis between the two tissues is formed.

Nonetheless, the difficulty of placing the magnets or couplings limits the locations that compressive anastomosis can be used. In most cases, the magnets or couplings have to be delivered as two separate assemblies, requiring either an open surgical field or a bulky delivery device. For example, existing magnetic compression devices are limited to structures small enough to be deployed with a delivery conduit e.g., an endoscopic instrument channel or laparoscopic port. When these smaller structures are used, the formed anastomosis is small and suffers from short-term patency.

Thus, there still remains a clinical need for reliable devices and minimally-invasive procedures that facilitate compression anastomosis formation between tissues in the human body.

SUMMARY

The invention provides improved devices and techniques for minimally-invasive formation of anastomoses within the body, e.g., the gastrointestinal tract. Such devices and techniques facilitate faster and less-expensive treatments for chronic diseases such as obesity and diabetes. Such techniques also reduce the time and pain associated with palliative treatments for diseases such as cancers such as stomach or colon cancer.

Using a combination of a guide element and an elongated manipulator or a guide element and a guide tube, magnetic anastomosis devices can be delivered to tissues, and then manipulated once delivered to the tissue, to achieve optimal placement and anastomosis formation. The devices allow for both endoscopic and laparoscopic delivery. For example, the invention includes a guide element coupled to a self-assembling magnetic anastomosis device and a guide tube that is used to push the self-assembling device from a delivery lumen and then place the device while viewing with an endoscope. In other instances, the invention includes a guide element coupled to a self-assembling magnetic anastomosis device and an elongated manipulator that is used to push the self-assembling device from a catheter and then place the device while viewing with a laparoscope. In both instances, the configuration allows a user to hold the device tightly for certain portions of the procedure, and also allow the device to move freely under gravity or magnetic attraction while maintaining a tether. This flexibility makes it easier to successfully mate with a complementary magnetic device, and it allows for adjustment of a deployed device when successful placement is not achieved.

In conjunction with the devices described herein, several surgical techniques are described for use with the device, including active patient manipulation and adding weight to the devices to improve manipulation.

In one aspect, the present invention includes a magnetic compression anastomosis device, shaped as a polygon or ring. The device includes magnetic segments that self-assemble into a geometric shape and radial members coupled to the polygon or ring and coupled to each other in proximity to a center point of the polygon or ring.

The radial members can be fabricated from a variety of materials to achieve the desired mechanical properties and bio-compatibility. The radial members may be constructed from metal, e.g., wire, e.g., stainless steel wire, or nickel alloy wire. The radial members may be constructed from natural fibers, such as cotton or an animal product. The radial members may be constructed from polymers, such as biodegradable polymers, such as polymers including repeating lactic acid, lactone, or glycolic acid units, such as polylactic acid (PLA). The radial members may also be constructed from high-tensile strength polymers, such as Tyvek™ (high-density polyethylene fibers) or Kevlar™ (para-aramid fibers). In an embodiment, the radial members 510 are constructed from biodegradable suture, such as VICRYL™ (polyglactin 910) suture available from Ethicon Corp., Somerville, N.J.

The radial members can be used in conjunction with a guide element to deliver and deploy the magnetic compression anastomosis device. For example, the radial members may be additionally coupled to a guide element that allows the center of a device to be placed in a desired location by manipulating the guide element. In particular, the device is adapted to be placed with an elongated manipulator coupled to the guide element. The magnetic device is configured to be delivered via at least one of a working channel of an endoscope, a trocar, cannula, catheter, or needle.

In one embodiment, the magnetic segments may be coupled end-to-end to define a linear assembly having first and second ends, and the linear assembly forms the polygon or ring by spontaneously joining the first and second ends. In another embodiment, the magnetic segments may be coupled end-to-end to define the polygon or ring, and the polygon or ring is collapsible to form a linear assembly having a length of approximately one half the perimeter of the polygon or ring.

The magnetic segments may generally be coupled together with an exoskeleton that directs the self-assembly. The exoskeleton may be formed from a resilient material. The resilient material may include metal or a polymer, such as, for example, a nickel alloy. At least one of the magnetic segments may be joined to an immediately adjacent magnetic segment by way of a mechanical connection.

In another aspect, the present invention includes a system for forming an anastomosis between adjacent tissues or organs. In particular embodiments, the tissues are adjacent gastrointestinal organs, such as, for example, the stomach and the gallbladder, the small intestine and the gallbladder, the stomach and the duodenum, or the ileum and the colon. The system includes an access device configured to provide access to an anatomical structure within a subject. For example, the access device may include an endoscopic or laparoscopic device, a trocar, cannula, catheter, or needle. The system further includes an elongate manipulator configured to fit within the access device and being independently translatable and rotatable relative to the device. The system further includes a magnetic compression anastomosis device, shaped as a polygon or ring, including radial members coupled to the polygon or ring and coupled to each other in proximity to a center point of the polygon or ring. The elongate manipulator is couplable to at least one radial member, thereby allowing the elongate manipulator to direct placement of the magnetic compression anastomosis device.

In some embodiments, the radial members and the elongated manipulator are coupled to at least one guide element. Accordingly, the radial members can be used in conjunction with the guide element and elongated manipulator to deliver and deploy the magnetic compression anastomosis device. For example, the radial members may be additionally coupled to the guide element that allows the center of a device to be placed in a desired location by manipulating the guide element via the elongated manipulator. The elongated manipulator may include a lumen having a distal and proximal end and the guide element may be disposed within the lumen and is translatable from a distal to a proximal position, as well as rotatable. The magnetic device is configured to be delivered via at least one of a working channel of an endoscope, a trocar, cannula, catheter, or needle.

In yet another aspect, the present invention provides a magnetic compression anastomosis system. The system includes a self-assembling magnetic compression device including magnetic segments, at least one guide element, having a proximal and a distal end, and coupled to the magnetic compression device, and a guide tube having a central lumen, wherein the guide element is positioned within the lumen and translation of the guide element causes translation of the magnetic compression device. The guide tube is sized to fit within at least one of a working channel of an access or delivery device, such as an endoscope, cannula, trocar, catheter, or needle. Furthermore, the guide tube is independently translatable and rotatable relative to the working channel of the access or delivery device. Accordingly, upon translation or rotation of the elongated manipulator, the magnetic compression device, one deployed and assembled, may correspondingly translate and/or rotate independently of the working channel of the access or delivery device.

When deployed in adjacent tissues, for example adjacent organs or different regions of the same organ, pairs of coupled magnetic devices create a compressive ring that can be surgically opened, or allowed to form an anastomosis without further intervention. When paired devices are left alone, the compressive force against the tissues collapse the vasculature and extrude fluids in the tissues, further reducing the distance between the devices and increasing the magnetic attraction. With time, the coupled devices eventually couple completely and fall away, leaving a formed anastomosis.

It should be noted that in some applications, pairs of magnetic devices can be used to create vascular anastomoses or to treat cardiac conditions. For example, a magnetic anastomosis coupling can be formed between adjacent blood vessels with magnetic devices. For example, a pair of magnetic devices can be delivered with a vascular delivery device, such as a catheter.

BRIEF DESCRIPTION OF THE DRAWINGS

FIG. 18A depicts manipulation of an anastomosis device coupled to a guide element and a guide tube;

FIG. 18B depicts manipulation of an anastomosis device coupled to a guide element and a guide tube;

FIG. 18C depicts manipulation of an anastomosis device coupled to a guide element and a guide tube;

DETAILED DESCRIPTION

The invention concerns delivering paired magnetic devices to either side of tissues to be joined. The magnetic anastomosis devices are coupled to a guide element that facilitates delivery and manipulation of the devices when using minimally-invasive techniques such as endoscopy and laparoscopy. Elongated manipulators and guide tubes can also improve a user's dexterity with the devices during placement. Once the devices have been placed and mated, the compressive forces cause the vasculature of the tissue to collapse and fluids to extrude from the tissues, reducing the distance between the devices and increasing the magnetic attraction. With time, the coupled devices eventually mate completely, form an opening, and fall away from the tissue, leaving an anastomosis. The magnetic devices can, thus, be used to create surgical-quality anastomosis without the need to create an open surgical field.

With this technique it is simpler to create openings between tissues that traditionally required open surgery or the use of complicated cutting and suturing devices. Most procedures are reduced to simply delivering a first magnetic compression device to a first tissue and then delivering a second magnetic compression device to a second tissue, and then bringing the two devices together. For example, it is straightforward to create a gastric bypass by delivering first and second magnetic devices, in the form of self-assembling octagons, to the stomach and the small intestine. The magnetic force of the two devices eventually creates an anastomosis that leads from the stomach to the small intestine, reducing the working volume of the stomach.

Overall, the design specifications of the devices depend on the patient and the intended anastomosis. The design specifications may include: required capture range, desired effective inner and outer diameters of the magnetic device (e.g., as defined by the desired anastomosis size and instrument passage), thickness of the target tissue, and the inner diameter of guiding channel and the smallest radius of curvature to which the guiding channel may be bent and through which the magnets must pass. Once the design specifications are chosen, corresponding magnetic device designs can be determined, such as polygon-side-count and length, and the maximum lateral dimensions of the flexible linear magnetic structure that will be deployed through the delivery instrument.

Figure 1:
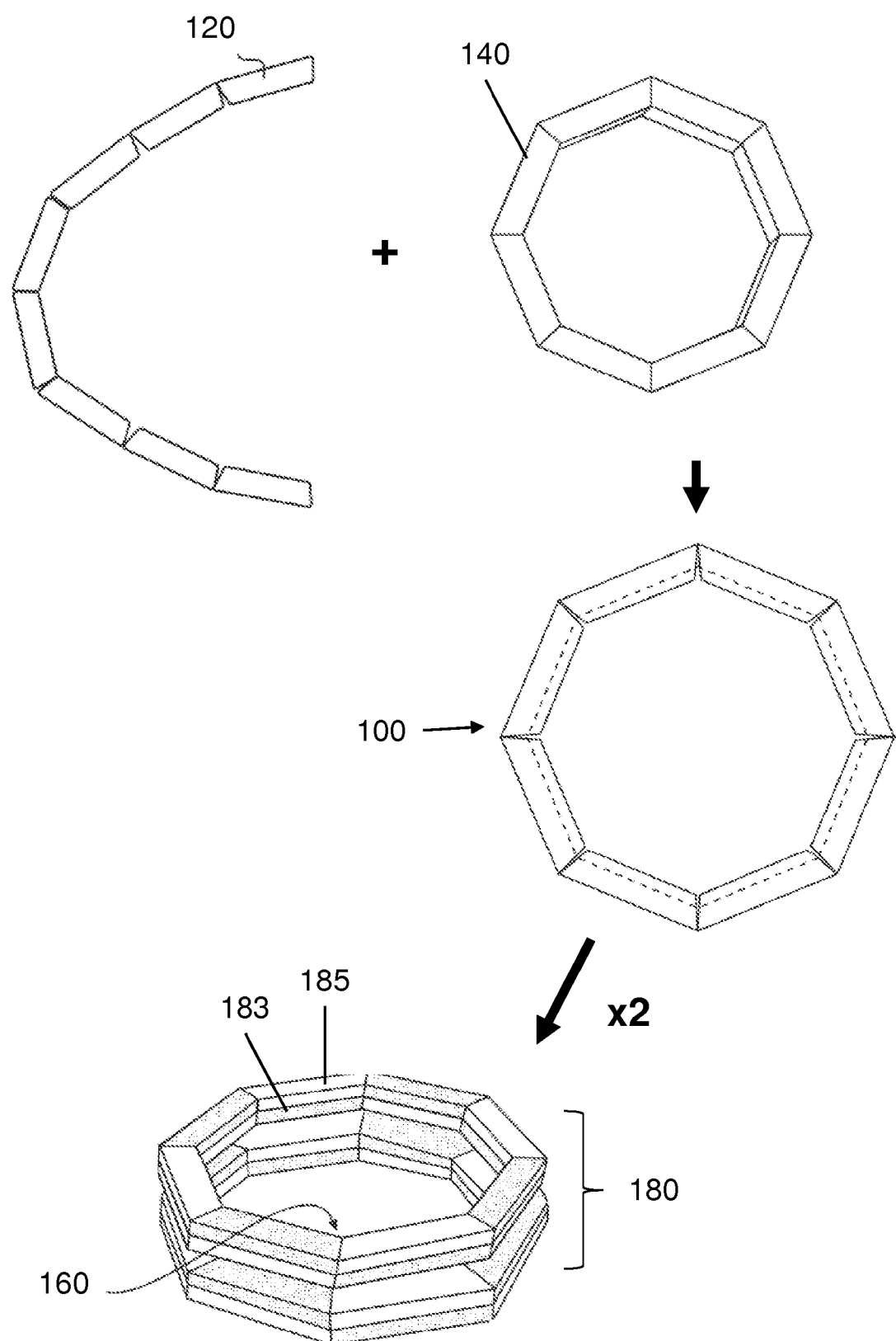
FIG. 1 depicts the formation of a self-assembling magnetic anastomosis device suitable for use with the devices, systems, and method of the invention.

The magnetic compression devices may be of several forms. For example, the magnetic compression devices may be ring-shaped or form an open polygon, such as a square, or a pentagon, or a hexagon, or an octagon, or another polygonal shape. An exemplary magnetic compression device, of the sort disclosed in U.S. 2013/0253550, incorporated herein by reference, is shown in FIG. 1. As shown in FIG. 1, self-assembling (i.e., self-forming) magnetic compression device 100 can be formed by delivering an exoskeleton 120 to a set of magnetic segments 140. The exoskeleton 120 may be made from a resilient material that will retain its shape after deformation, such as a polymer or metal alloy. In some embodiments, the metal alloy will comprise nickel, such as nitinol. The magnetic segments 140 may be comprised of any strongly-magnetic material, such as rare earth magnetics, comprising materials such as neodymium, samarium, erbium, yttrium, ytterbium, and cobalt. In some embodiments, the magnetic segments may be coated, e.g., with gold or Teflon, to improve durability or biocompatibility. Once assembled, the resulting self-assembling magnetic anastomosis device can be intentionally deformed into a semi-linear shape, but will form a polygon when released as shown in FIG. 1.

As described herein, the magnetic devices are relatively smooth and flat and have essentially uninterrupted annular faces. Because of this design, the devices do not cut or perforate tissue but rather achieve anastomosis by providing steady necrotizing pressure across the contact surface between mating polygonal rings. These features also reduce the risks associated with surgical access and ensure that the anastomosis is formed with the correct geometric attributes. Overall, this ensures the patency of the anastomosis.

As show in FIG. 1, two self-assembling magnetic compression devices 100 can be associated as a matched set 180. As described above, tissues that are trapped between the matched set 180 will be compressed, and eventually grow together, leaving an opening 160 in the tissue. As shown in FIG. 1, each magnetic segment of the matched set 180, has at least at least two poles 183 and 185, with the poles oriented normal to the face of the polygon. When assembled, the poles of the segments in adjoining devices are arranged N/S/N/S or S/N/S/N. The aligned and matching poles in the matched set 180 form a very strong coupling between the two elements. Additionally, the attractive forces between opposing poles of nearby magnetic segments facilitates assembly of matched set 180. Typically, the two elements of the matched set 180 need only to be placed in proximity to each other and the magnetic segments will self-align in the preferred configuration. In some instances, it is necessary to pre-align the complimentary devices, however, in other instances the devices self-align by undergoing fast in-plane rotation with respect to one another.

In some embodiments, the invention includes flexible linear magnetic devices comprising linked magnetic multi-pole segments that self-assemble to form a polygon when extruded from the and of a delivery lumen, e.g., through a trocar or a working channel of an endoscope 200, as shown in FIGS. 2-24. As each successive magnetic segment emerges from the end of the guiding channel into the organ lumen, the exoskeleton constrains the segment against out-of-polygonal plane deflection and the segments' mutual attractions close each miter joint in the correct inward direction, sequentially correct and, as the last segment is extruded, to close the polygonal magnetic ring. Although the exoskeletal bias and out-of-polygonal-plane stiffness is important for guiding the miter closure, the principle motive and retentive force is the magnetic attraction of the miter surfaces, by virtue of their opposite magnetic polarity. The strength of this interaction, i.e., the depth of the potential energy well into which the attracted surfaces fall, contributes to the physical integrity and stability of the polygonal ring magnet device. Furthermore, when the devices are constructed with symmetric miter joints and have their magnetic poles aligned with the annular axis of the polygon, the total magnetic force normal to the mating surfaces is maximized. The magnetic forces increase the mechanical stability of a set of coupled magnets while speeding anastomosis formation due to the intense compressive force on the trapped tissues.

During deployment, the exoskeletal hinge between magnetic segments couples the structural rigidity of individual segments similar to a cantilevered beam. In other words, the tensile modulus of the exoskeleton and the exoskeleton's resistance to out-of-plane bending allow the forces on the distal end of the structure to be distributed across the magnetic segments. The design allows a pushing force on the proximal end of the device to reliably move the distal end of the device, e.g., out of the deployment lumen. Because the exoskeleton is thin and in close contact with the magnetic segments that are long relative to the length of the miter joint, the exoskeleton can bend to accommodate miter closure with relatively small strain. However, the breadth of the exoskeleton produces a high moment of inertia (stiffness) against out-of-polygonal-plane bending, thereby giving good guidance of the growing ring and providing lateral resistance to deflection during closure. Finally, the exoskeleton also provides a tensile coupling between the magnetic segments, assuring that the segments do not go past the closure point and collapse inward or over top of one-another.

Figure 2:
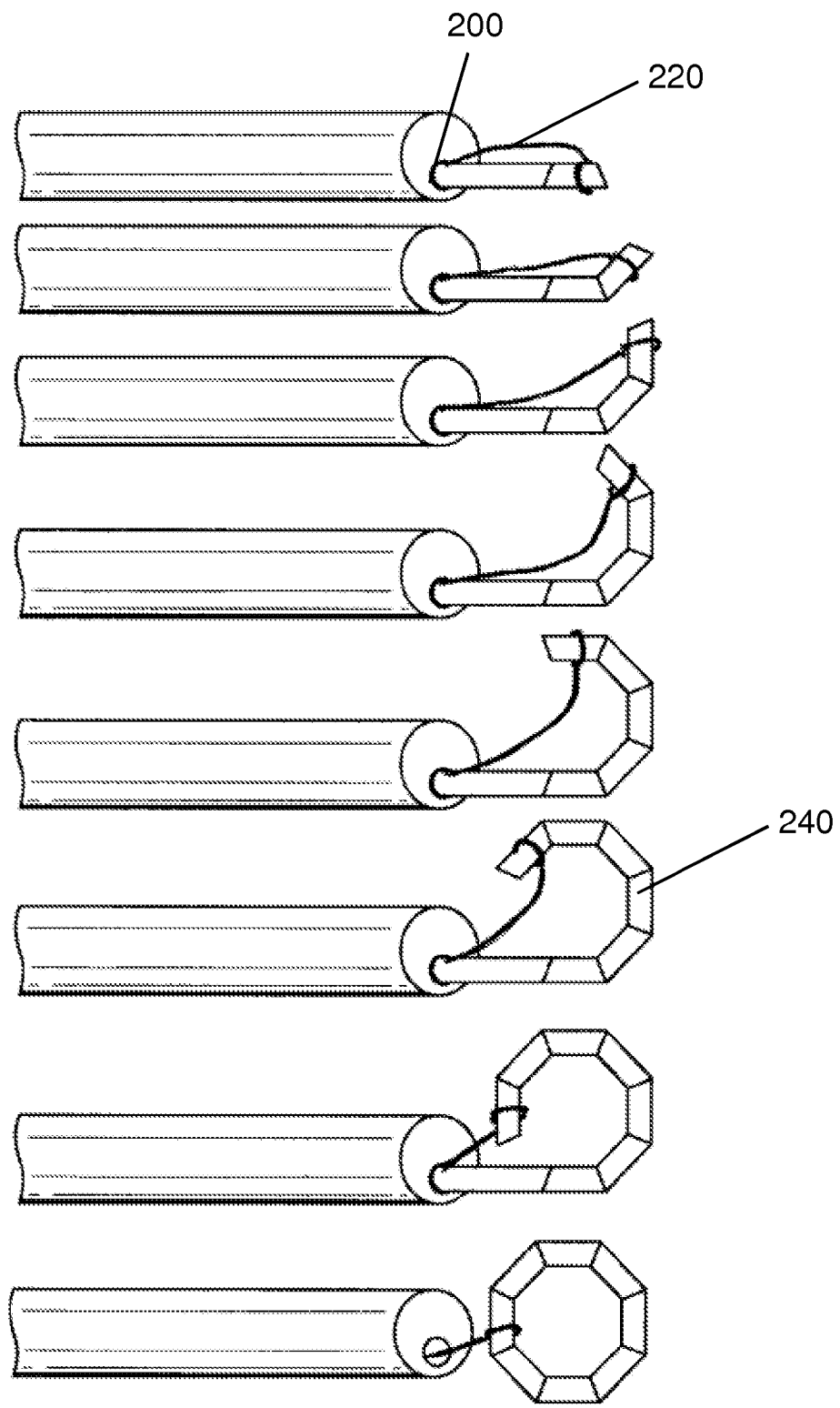
FIG. 2 depicts an embodiment of the invention including a guide element for deploying a magnetic anastomosis device.

Once the self-assembling magnetic device has been delivered to a tissue, it is beneficial to be able to manipulate the location of the device 240. While the device 240 can be manipulated with conventional tools such as forceps, it is often simpler to manipulate the location of the deployed device 240 with a guide element 220, such as a suture or wire. As shown in FIGS. 2-5, a variety of attachment points can be used to provide control over the location and deployment of a self-assembling magnetic anastomosis device 240. For example, as shown in FIG. 2, the guide element may be coupled to a single distal segment such that, upon self-assembly, the single distal segment results in an attachment point that provides translational freedom of movement. It is also notable that the configuration shown in FIG. 2 also allows a closing force to be applied to the distal-most segment. That is, in the event that one or more segments should become entangled with tissue, or otherwise prevented from self-assembling, a proximal pulling force with the guide element 220 can help the device 240 to complete self-assembly. Once self-assembly is completed, the device 240 can be positioned with the guide element 220 to be mated with another device (not shown) to form an anastomosis, as described above. While it is not shown in FIG. 2, it is envisioned that additional structures, such as a solid pusher or a guide tube can be used to deploy the device 240 in the desired location. Greater details of the delivery pusher and guide tube are provided below.

The guide element 220 can be fabricated from a variety of materials to achieve the desired mechanical properties and bio-compatibility. The guide element 220 may be constructed from metal, e.g., wire, e.g., stainless steel wire, or nickel alloy wire. The guide element may be constructed from natural fibers, such as cotton or an animal product. The guide element may be constructed from polymers, such as biodegradable polymers, such as polymers including repeating lactic acid, lactone, or glycolic acid units, such as polylactic acid (PLA). The guide element may also be constructed from high-tensile strength polymers, such as Tyvek™ (high-density polyethylene fibers) or Kevlar™ (para-aramid fibers). In an embodiment, guide element 220 is constructed from biodegradable suture, such as VICRYL™ (polyglactin 910) suture available from Ethicon Corp., Somerville, N.J.

Figure 3:
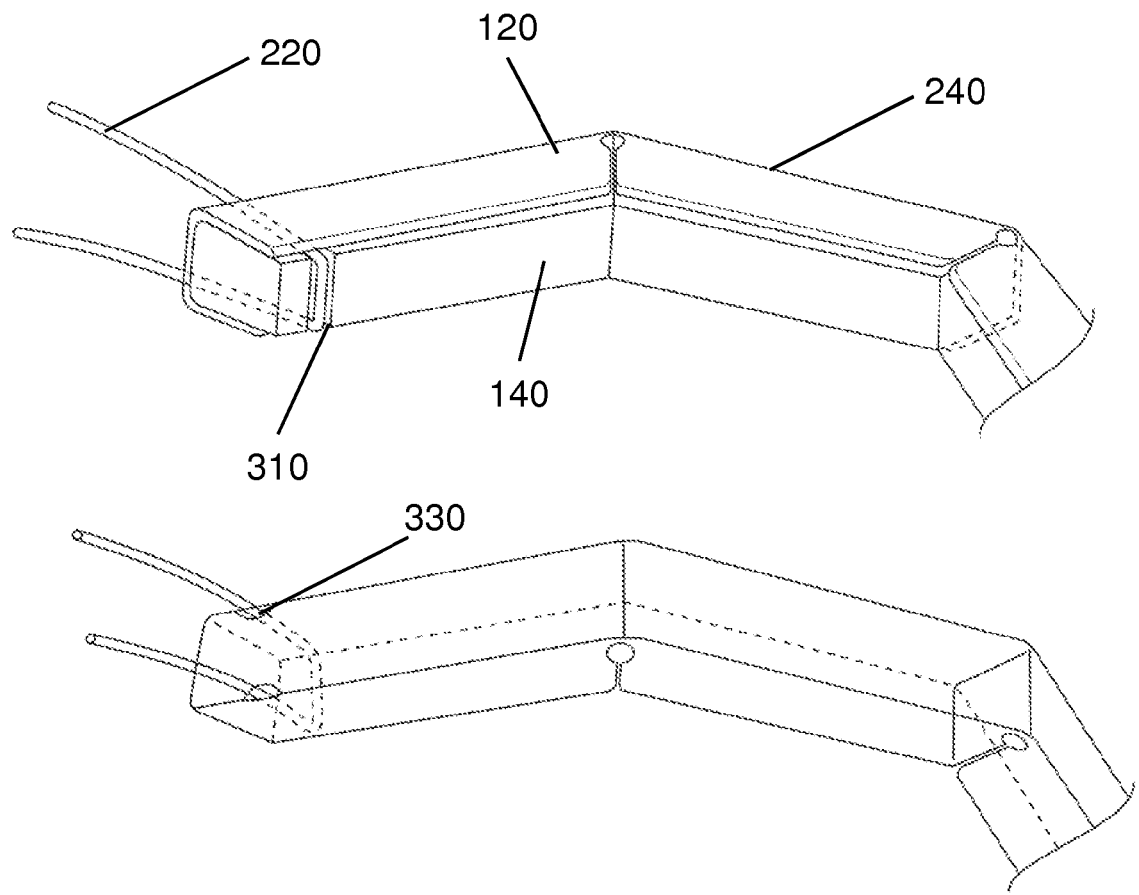
FIG. 3 illustrates a method for attaching a guide element to an anastomosis device.

The guide element 220 can be coupled to the self-assembling magnetic anastomosis device 240 with a number of different configurations and attachment mechanisms. The guide element 220 may be simply tied to the device 240, or the guide element 220 can be attached to the device 240 with an adhesive, e.g., acrylate glue, or with a fastener, such as a clip, screw, or rivet. An exemplary configuration of the guide element 220 connected to the device 240 is shown in FIG. 3, whereby the guide element 220 is placed in a channel 310 in a magnetic segment 140, and then the exoskeleton 120 is formed or placed around the magnetic segment 140 entrapping the guide element. The guide element 220 emerges from an opening 330 in the exoskeleton 120, thus assuring that the guide element 220 does not interfere with the mating between devices 240.

Figure 4:
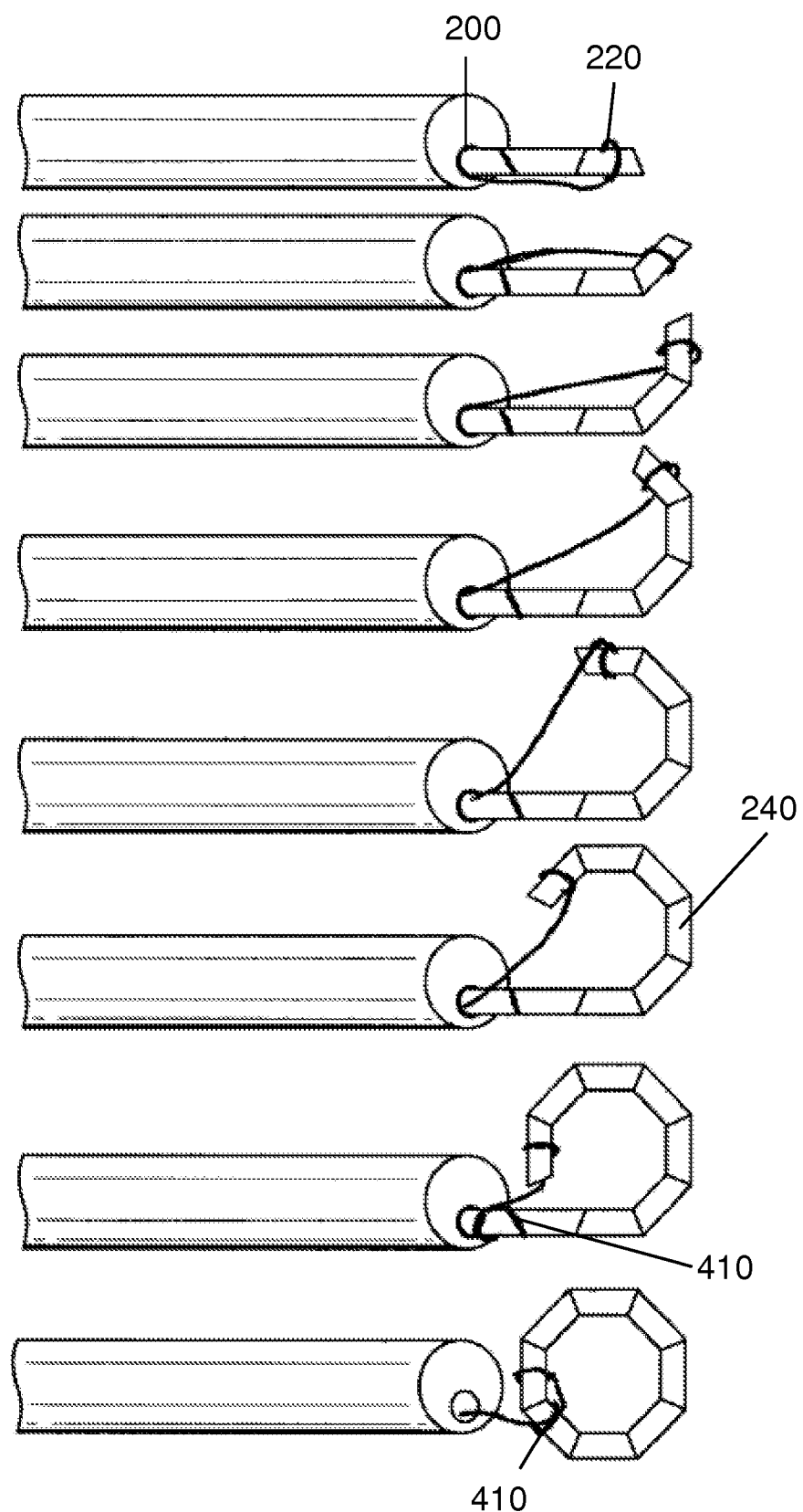
FIG. 4 depicts an embodiment of the invention including a guide element for deploying a magnetic anastomosis device.
Figure 5:
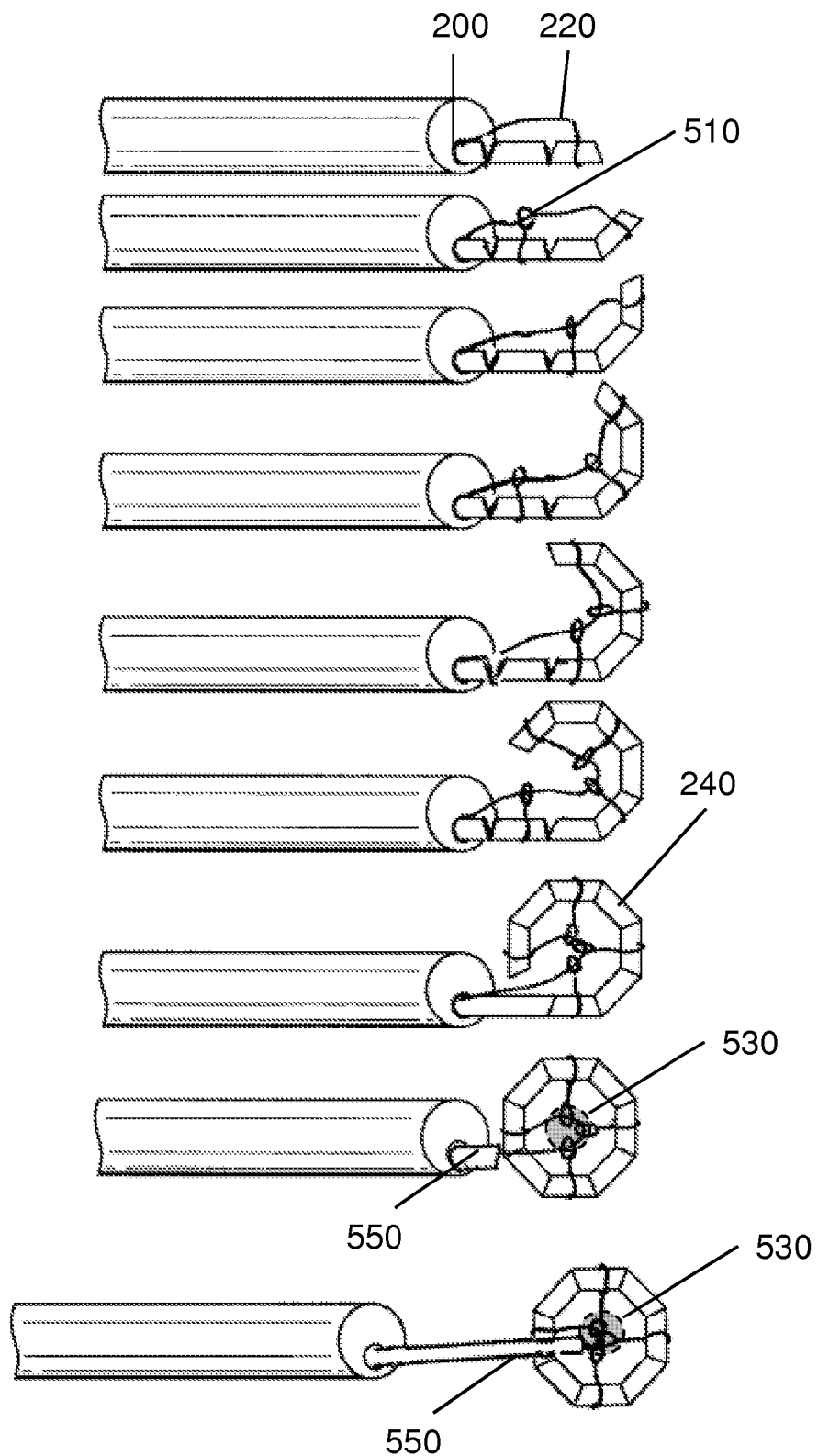
FIG. 5 depicts an embodiment of the invention including radial members and a guide element for deploying a magnetic anastomosis device.

In other embodiments, such as shown in FIGS. 4 and 5, the guide element 220 may be attached to, or configured to interact with, more than one part of the device 240. As shown in FIG. 4, the guide element 220 may be attached to the distal-most segment of a self-assembling device 240, and also interact with a restraint 410 affixed to the proximal-most segment of the device 240. As the self-assembling device 240 is deployed from lumen 200, a proximal force on the guide element 220 will cause the distal and proximal ends of the device 240 to join, thus forming a completed polygon. The guide element 220 can also be used to place the assembled device 240. While it is not shown in FIG. 4, it is envisioned that additional structures, such as an elongated manipulator or a guide tube can be used to deploy the device 240 in the desired location. Greater details of the elongated manipulator and guide tube are provided below.

FIG. 5 shows another embodiment of the invention, wherein a guide element 220 is coupled to the distal-most segment of a self-assembling device 240, and configured to interact with radial members 510 that facilitate assembly and placement of the device 240. As shown in FIG. 5, proximal force on the guide element 220 helps the device 240 to self-assemble. As shown in FIG. 5, the radial members 510 also establish a center 530 of the device, which is coupled to the guide element 220 when the device 240 has assembled and the guide element 220 is pulled taut. The center 530 of the device 240 can then be delivered to a desired location, e.g., opposite a mating device on the other side of a tissue.

The radial members 510 can be fabricated from a variety of materials to achieve the desired mechanical properties and bio-compatibility. The radial members 510 may be constructed from metal, e.g., wire, e.g., stainless steel wire, or nickel alloy wire. The radial members 510 may be constructed from natural fibers, such as cotton or an animal product. The radial members 510 may be constructed from polymers, such as biodegradable polymers, such as polymers including repeating lactic acid, lactone, or glycolic acid units, such as polylactic acid (PLA). The radial members 510 may also be constructed from high-tensile strength polymers, such as Tyvek™ (high-density polyethylene fibers) or Kevlar™ (pam-aramid fibers). In an embodiment, the radial members 510 are constructed from biodegradable suture, such as VICRYL™ (polyglactin 910) suture available from Ethicon Corp., Somerville, N.J. While the radial members 510 are depicted with a self-assembling device 240 in FIG. 5, it is to be understood that the radial members 510 can be used in conjunction with a guide element 220 to deliver and deploy anastomosis devices, generally, that are in the shape of a polygon or ring.

In several embodiments of the invention, a device, e.g., a self-assembling magnetic device is delivered with an elongated manipulator or guide tube. FIG. 5 additionally exemplifies a guide tube 550 that is used to deploy and place the device 240. The guide tube 550 can be constructed from any biocompatible material, and includes a lumen (not shown in FIG. 5) to allow the guide element 220 to pass through the guide tube 550, thus allowing manipulation of the guide element 220 independently of the guide tube 550. Typically, the guide tube 550 is formed from a semi-flexible or flexible material, thus allowing the guide tube 550 to be delivered via a flexible lumen 200, such as the working channel of an endoscope. Other methods of delivery with the guide tube 550, such as through a catheter or port are also possible. In a preferred embodiment, the guide tube 550 is constructed from a non-magnetic material so that the guide tube 550 is not attracted to the strong magnetic segments of a device 240.

As shown in FIG. 5, the guide tube 550 helps to push the device 240 out of the lumen 200. Once the device 240 is has been deployed, the center 530 of the device 240 can be placed with the tip of the guide tube 550. As show in FIG. 5, the guide tube 550 has a lumen (not shown) to allow the guide element 220 to span the length of the guide tube 550. As shown in FIG. 5, because the device 240 remains coupled to the guide element 220 when the guide tube 550 is removed, it is possible to re-engage the center 530 of the device with the guide tube 550 after the guide tube 550 has been withdrawn from the center 530. That is, it is possible to quickly access several combinations of center 530/guide tube 550/guide element 220 configurations, such as "tight hold" wherein the guide tube 550 is adjacent the center 530 and the guide element 220 is pulled taut against the radial members 510 (bottom drawing of FIG. 5) or "loose hold" where the guide tube 550 has been moved proximally away from the center 530, and the guide element 220 is allowed to slacken between the lumen 200 and the center 530. The "loose hold" position may be beneficial when mating two magnetic devices. The "loose hold" position allows a user to manipulate the body of the patient to achieve an optimal position for coupling two elements without concern for damaging tissue with an extended guide tube 550. In the event that it is not possible to position the device 240 using the "loose hold," however, it is possible to re-engage the center 530 and move the device 240 with the guide tube 550 (see also FIGS. 18A-18F). It should be noted that other configurations are also possible. For example, a device 240 may have first and second guide elements 220 coupled to two segments of a magnetic anastomosis device, providing means for steering, rotating, or manipulating a deployed device 240.

Figure 6:
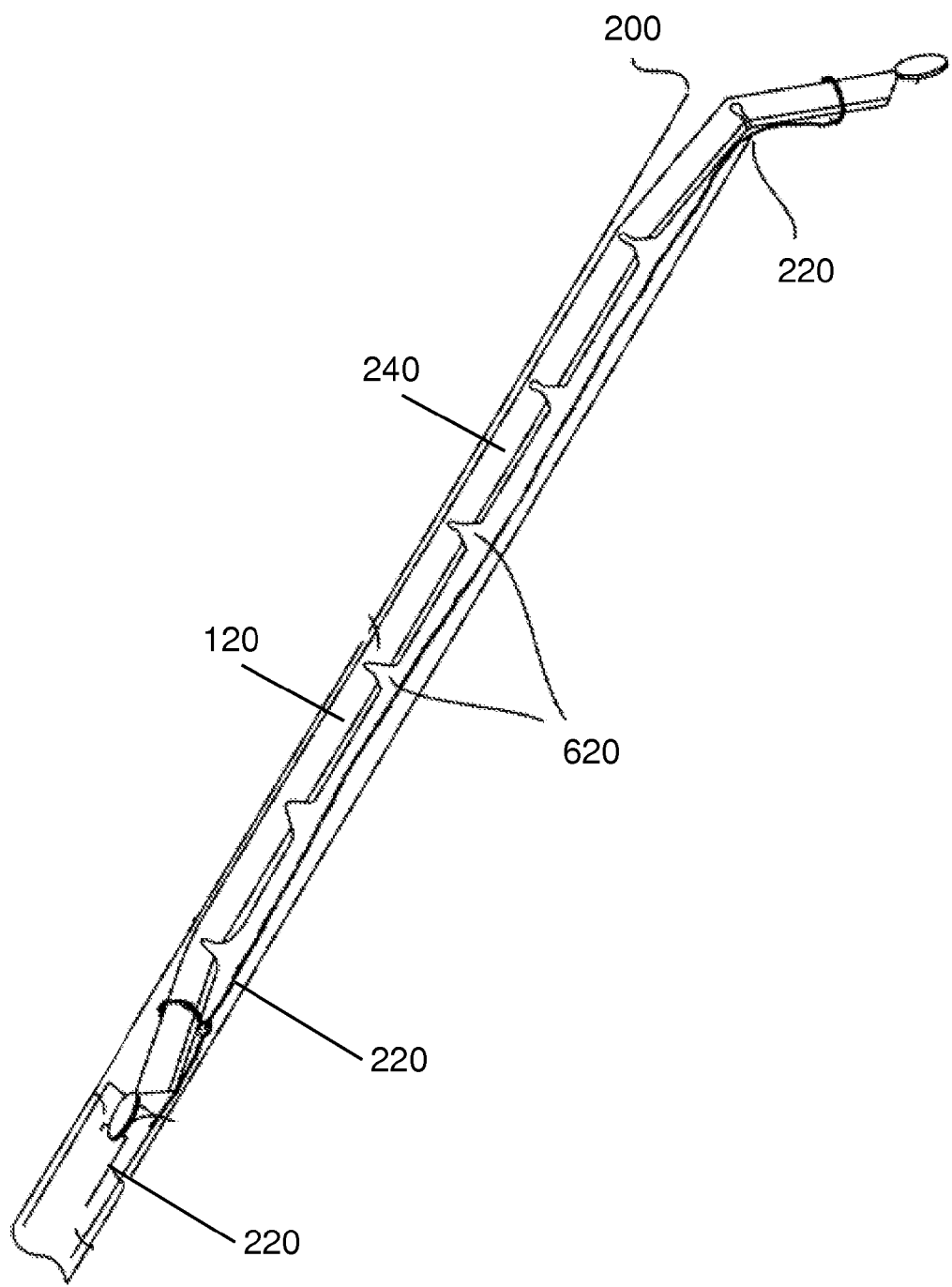
FIG. 6 is a cut-away of the delivery lumen depicted in FIG. 4.
Figure 7:
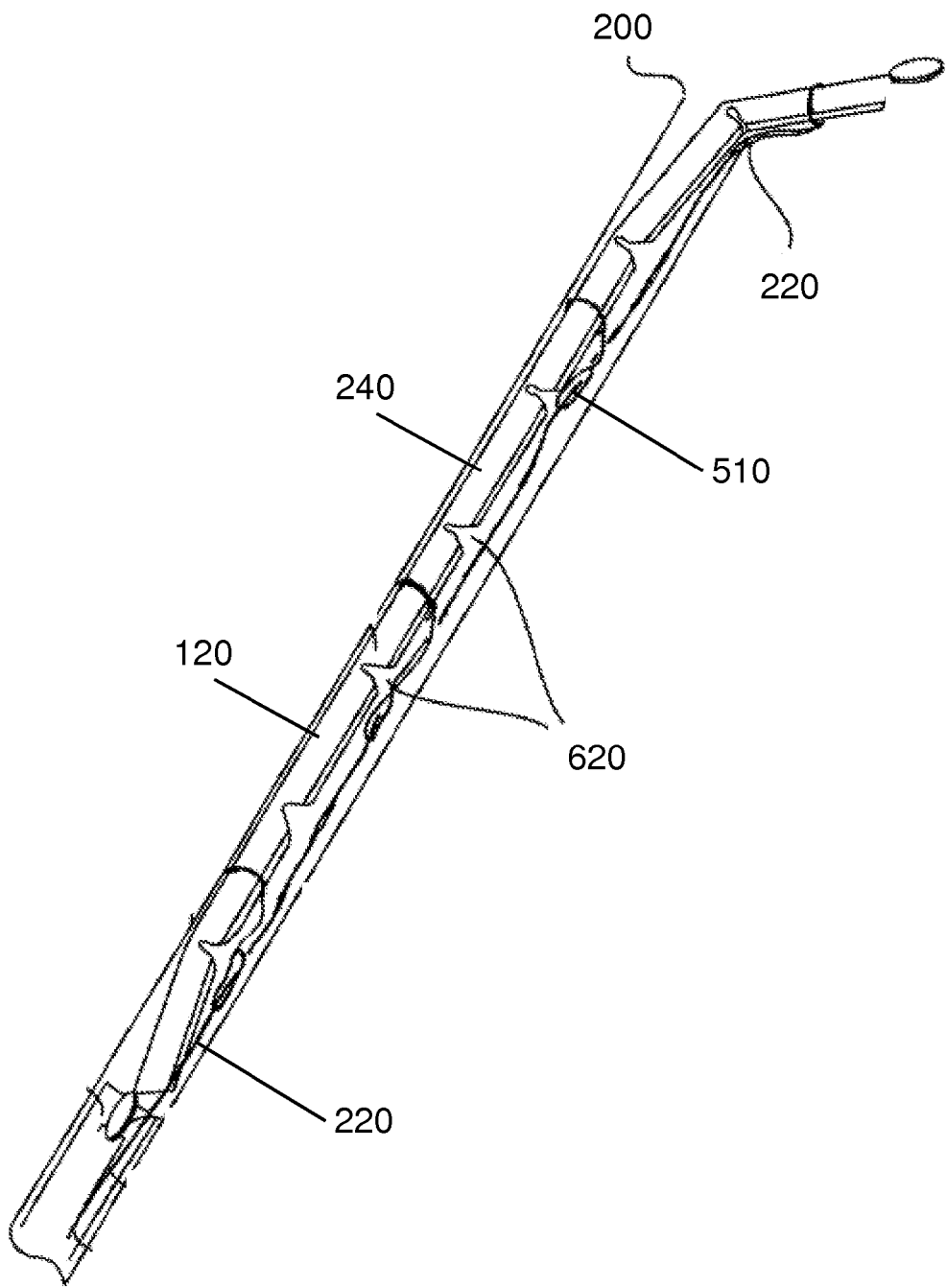
FIG. 7 is a cut-away of the delivery lumen depicted in FIG. 5.

A cross-section of lumen 200 of FIG. 4 is shown in FIG. 6 and a cross-section of lumen 200 of FIG. 5 is shown in FIG. 7. In FIGS. 6 and 7, the self-assembling device 240 is shown in a substantially linear configuration whereby the magnetic segments 140 (hidden in FIGS. 6 and 7) are separated by gaps 620, but the magnetic segments 140 are kept together by exoskeleton 120. Because the exoskeleton 120 is made of a resilient material, the device 240 will naturally self-assemble after being held in the substantially linear configuration shown in FIGS. 6 and 7. As shown in FIG. 6, the guide element 220 is coupled to the distal and proximal ends of the device, and the guide element 220 runs the length of the lumen 200 and extends proximally past the device 240. As shown in FIG. 7, the guide element 220 is coupled to the radial members 510 that are stowed within the lumen 200 while coupled to the device 240. As the device 240 is pushed out of the lumen 240, e.g., with guide tube 550 (not shown in FIG. 6 or 7), the device 240 self-assembles as shown in FIG. 5, and the center 530 is defined as the common location of the radial members 510 and the guide element 220.

Figure 8:
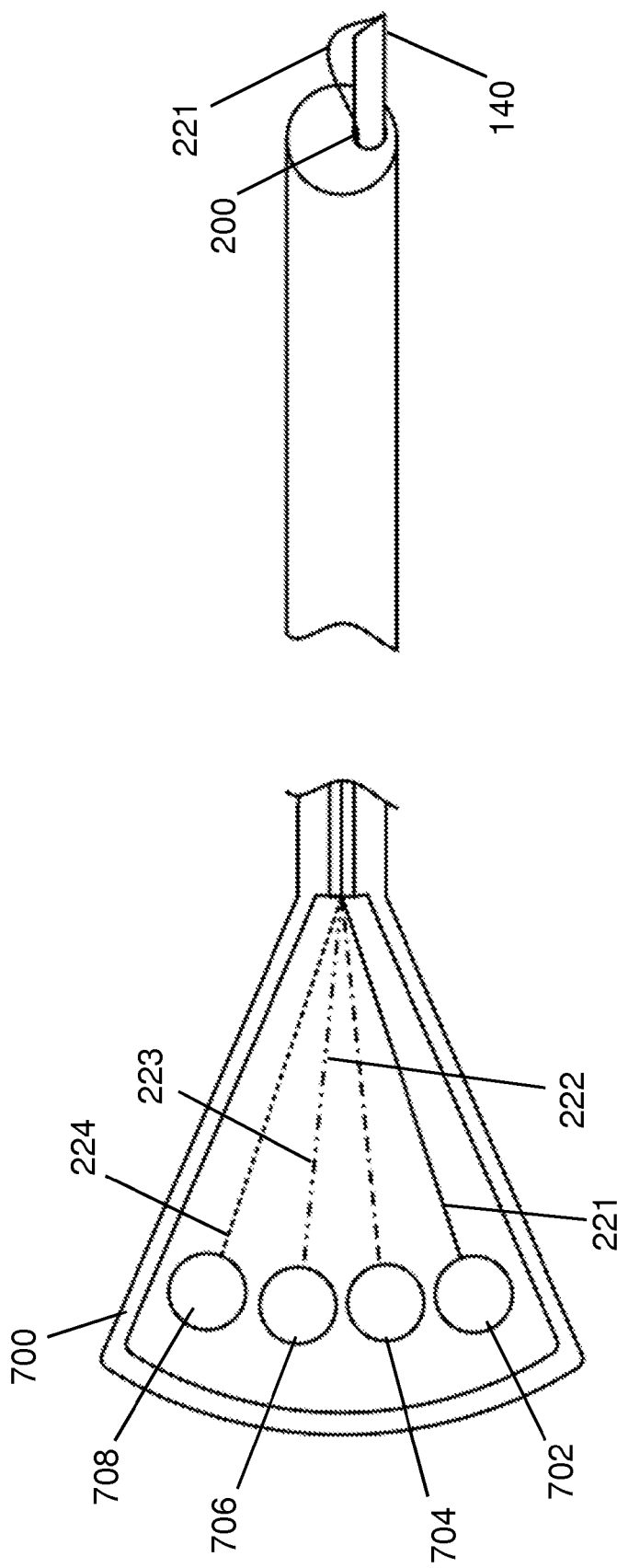
FIG. 8 is a tensioner that may be used with devices, systems, and methods of the invention.

FIG. 8 is a tensioner member 700 that may be used with devices, systems, and methods of the invention. As will be described in greater detail herein, the tensioner 700 is configured to keep one or more guide elements taught during delivery and self-closing of a magnetic device 240 consistent with the present disclosure. As previously described, once the self-assembling magnetic device has been delivered to a tissue, it is beneficial to be able to manipulate the location of the device 240. While the device 240 can be manipulated with conventional tools such as forceps, it is often simpler to manipulate the location of the deployed device 240 with one or more guide elements 220. In the embodiment shown in FIGS. 8-15, significant tension can be applied upon one or more magnetic segments 140 via a tensioner 700 configured to provide a user or operator with handheld control over one or more guide elements coupled to the magnetic segments 140. For example, as shown in FIG. 8, the tensioner 700 includes control members 702-710 for providing a user with control over the tension of guide elements 221-224 coupled thereto, respectively, and thereby allows tension to be applied to magnetic segments to which the guide elements are coupled. As shown, the control members 702-710 may generally be in the form rings for receiving a user's fingers, for example. As will be described in greater detail herein, the control members may each be individually manipulated and further transition between locked and unlocked states. The application of tension generally eliminates slack during self-closing or self-opening, keeps the guide elements out of the way of visualization or other procedures, and further stabilizes the device during transition from delivery state to deployed state.

Figure 9:
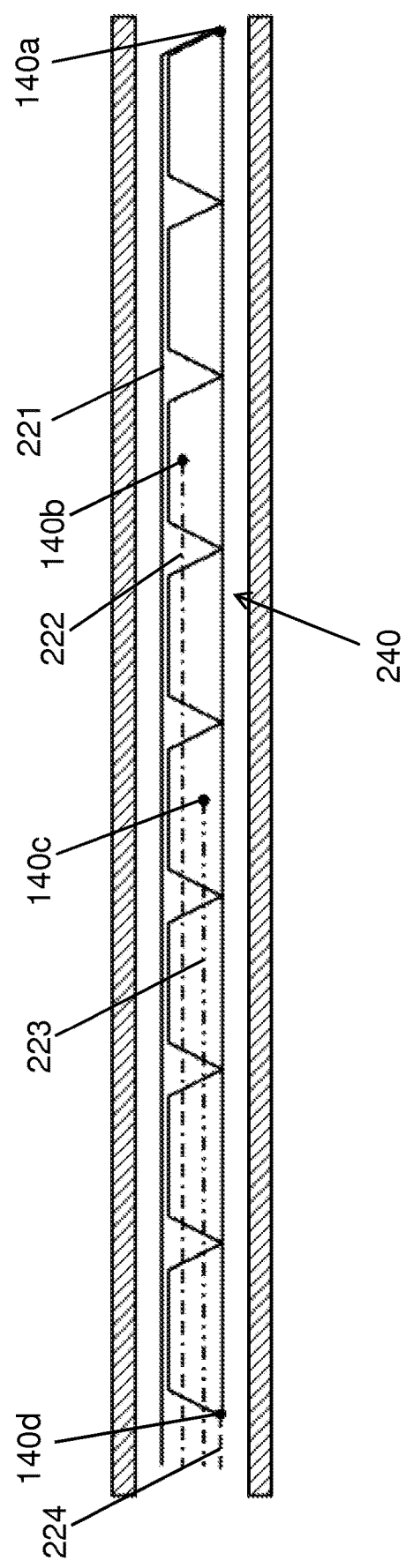
FIG. 9 depicts a side view of a self-closing magnetic anastomosis device including a plurality of guide elements for deploying the anastomosis device with the tensioner of FIG. 8.
Figure 10:
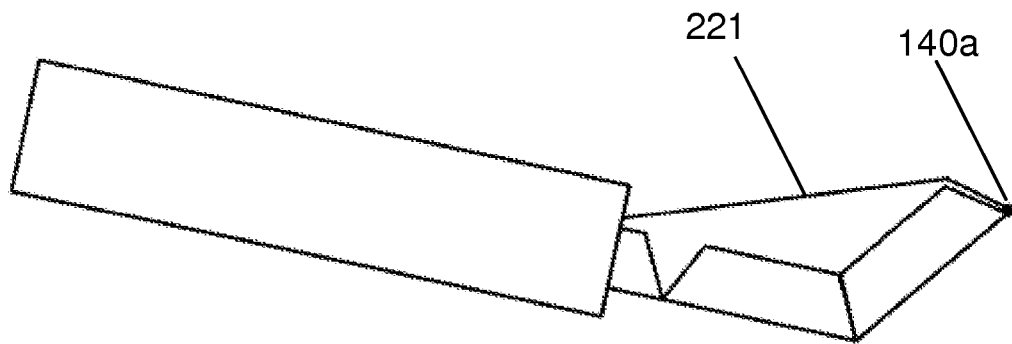
FIGS. 10, 11, 12, 13, and 14 each depict the deployment of the self-closing magnetic anastomosis device with the tensioner and plurality of guide elements.
Figure 11:
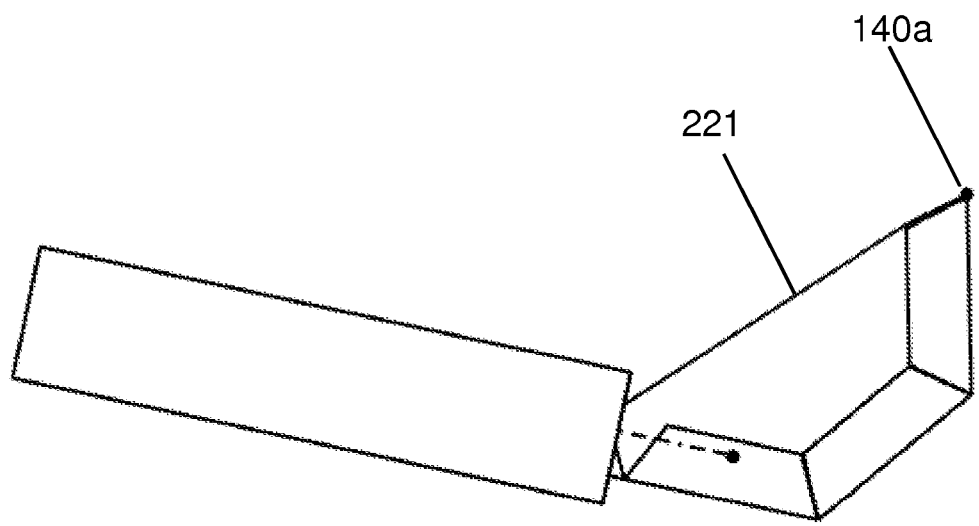
Figure 12:
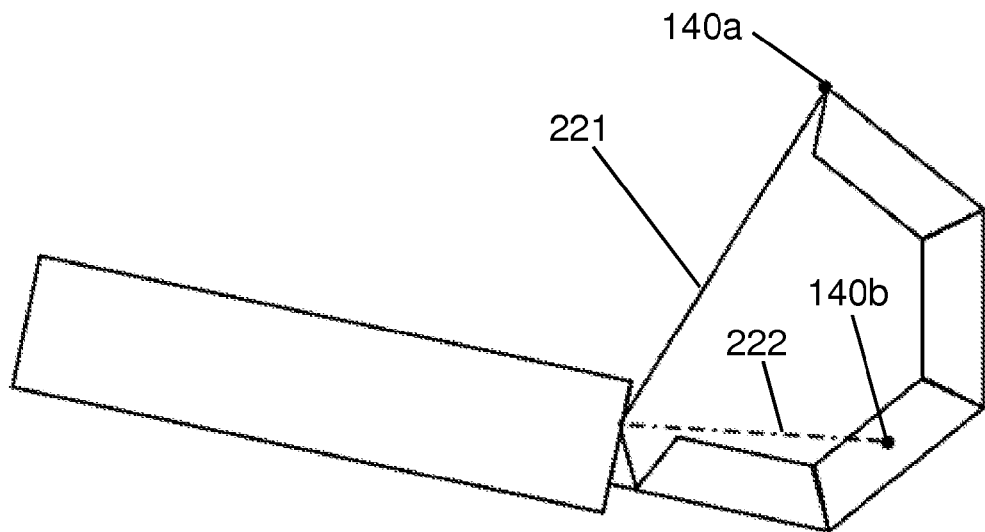
Figure 13:
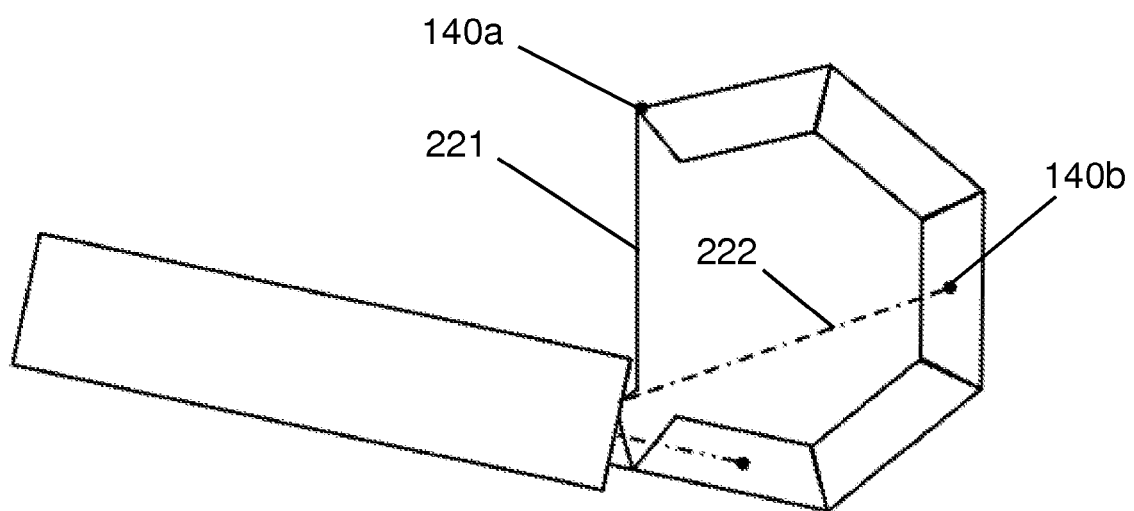

A cross-section of lumen 200 of an endoscope, trocar, or other delivery device described herein, is shown in FIG. 9. In FIG. 9, the self-assembling device 240 is shown in a substantially linear configuration. As previously described, a variety of attachment points can be used to provide control over the location and deployment of a self-assembling magnetic anastomosis device 240. As shown in FIGS. 9-15, for example, four guide elements 221-224 may be coupled to four separate segments 140a-140d of the device 240, respectively. Accordingly, the guide elements 221, 222, 223, and 224 are coupled to the control members 702, 704, 706, and 708, respectively, such that, upon manipulation of a control member, a user may apply (or loosen) tension of a guide element and thus manipulate the associated magnetic segment coupled thereto. As shown, guide element 221 is coupled to the most distal end segment 140a, guide elements 222 and 223 are coupled to segments 140b and 140c, respectively, and guide element 224 is coupled to the most proximal end segment 140d.

The guide elements 221-224 can be fabricated from a variety of materials to achieve the desired mechanical properties and bio-compatibility. The guide elements 221-224 may be constructed from metal, e.g., wire, e.g., stainless steel wire, or nickel alloy wire. The guide elements may be constructed from natural fibers, such as cotton or an animal product. The guide elements may be constructed from polymers, such as biodegradable polymers, such as polymers including repeating lactic acid, lactone, or glycolic acid units, such as polylactic acid (PLA). The guide elements may also be constructed from high-tensile strength polymers, such as Tyvek™ (high-density polyethylene fibers) or Kevlar™ (para-aramid fibers). In an embodiment, guide elements 221-224 are constructed from biodegradable suture, such as VICRYL™ (polyglactin 910) suture available from Ethicon Corp., Somerville, N.J.

The guide elements 221-224 can be coupled to the segments 140a-140d of the self-assembling magnetic anastomosis device 240 with a number of different configurations and attachment mechanisms. The guide elements may be simply tied to de device 240, or the guide elements 221-224 can be attached to the device 240 with an adhesive, e.g., acrylate glue, or with a fastener, such as a clip, screw, or rivet.

Figure 14:
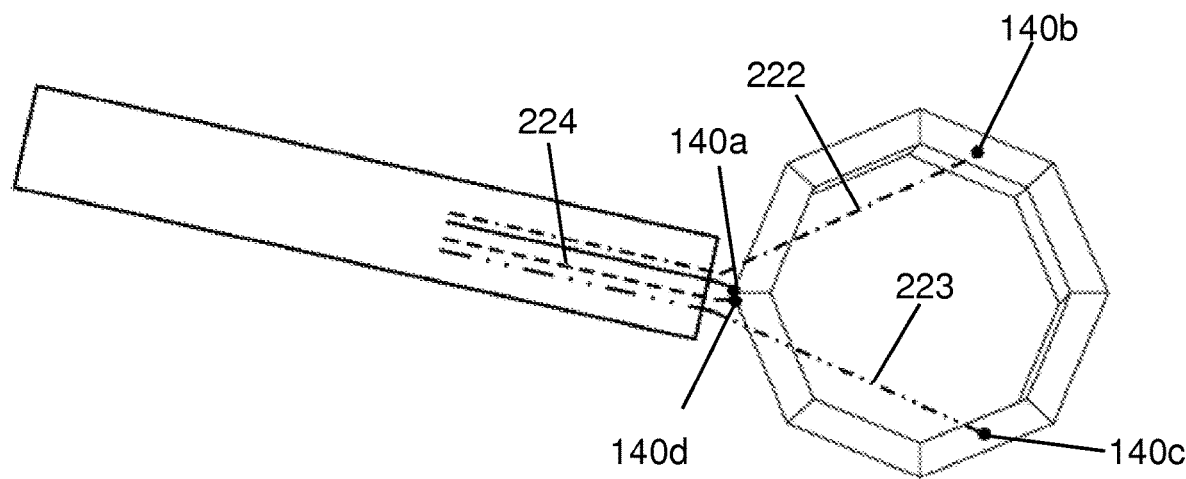

FIGS. 10-14 depict the deployment of the self-closing magnetic anastomosis device with the tensioner and plurality of guide elements. The delivery and deployment of a device 240 begins by advancing a pusher, for example, with tension on at least guide element 221. As the magnetic segments 140 are expelled from the lumen 200, the tension upon guide element 221 forces the most distal end segment 140a to begin assembly of the device 240. Further, tension upon guide element 224 forces the most proximal end segment 140d into contact with the most distal end segment 140a so that the device 240 is assembled. A user may then lock a respective control member 702-708 on the tensioner 700 so as to maintain the tension upon the respective guide element. For example, a taught guide element 221 has the potential of deflecting tissue folds from inadvertent capture, as well as assuring a tight 'turning radius' within the intestinal lumen that has, heretofore, been assured by the eight attractive miters of the device 240. Once the most distal and proximal end segments 140a, 140d are pulled by guide elements 221, 224 within their capture distance, the segments 140a and 140d close-range attraction can dominate the other repulsions and close the ring gap, as shown in FIG. 14. The ring may be quite oval, but it is closed. At this point, the other guide elements 222 and 223 may be used to tighten the polygon and correct any deflection or mismatch. By locking the guide elements 221-224, lateral deflection of the exposed length of a guide element can apply appropriate tensions. Once deployed, the tensioned guide wires can be used for aligning and mating a magnetic set. This may be visualized using fluoroscopy.

Figure 15:
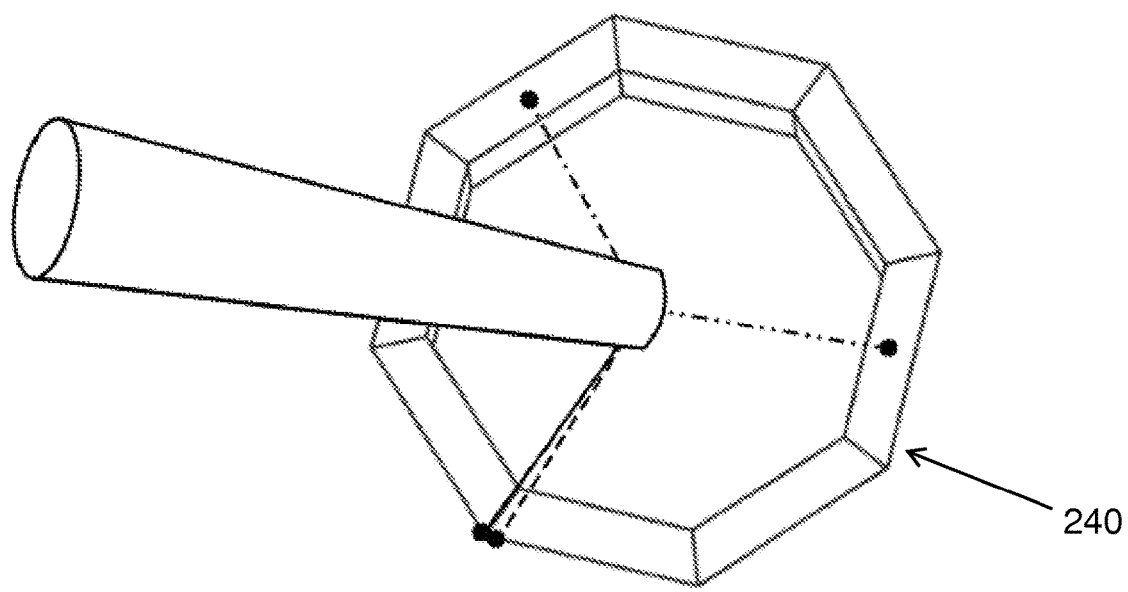
FIG. 15 depicts manipulation of the deployed self-closing magnetic anastomosis device of FIG. 14.

FIG. 15 depicts manipulation of the deployed self-closing magnetic anastomosis device 240 of FIG. 14. Once self-assembly is completed, the device 240 can be positioned with the guide elements 221-224 to be mated with another device (not shown) to form an anastomosis, as described above. Furthermore, a solid pusher or a guide tube can be used to deploy the device 240 in the desired location.

Figure 16:
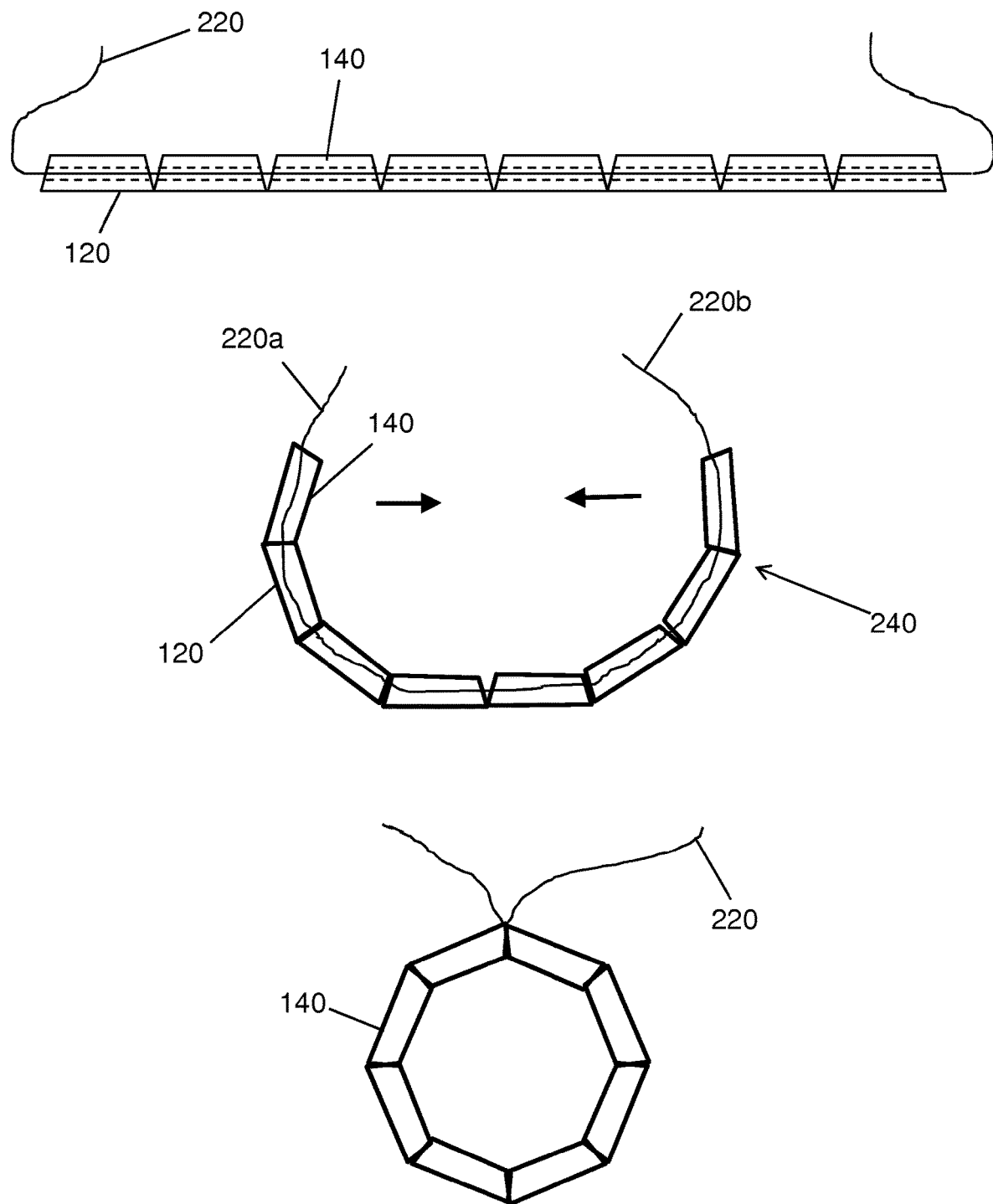
FIG. 16 depicts a self-closing magnetic anastomosis device suitable for use with the devices, systems, and methods of the invention.

FIG. 16 depicts a self-closing magnetic anastomosis device suitable for use with the devices, systems, and method of the invention for forming an anastomosis. The device includes a central member, which may be similar to guide element 220, to couple the magnetic segments 140 to one another. The central member may also facilitate placement of the device 240. As shown in FIG. 16, the self-closing device 240 may generally include a series of lumens through the magnetic segments 140 to allow a central member to be run through the magnetic segments 140 to facilitate assembly. The central member can be fabricated from a variety of materials to achieve the desired mechanical properties and bio-compatibility. For example, the central member may be constructed from metal, e.g., wire, e.g., stainless steel wire, or nickel alloy wire.

In some embodiments, the central member may be thermally-programmed so as to assume the desired shape, e.g., a circle, when exposed to body temperature, for example. Accordingly, the central member may be a wire, such as a stainless steel or nitinol wire. In other embodiments, the central member may be constructed from suture, wherein the central member may be constructed from natural fibers, such as cotton or an animal product or from polymers, such as biodegradable polymers, such as polymers including repeating lactic acid, lactone, or glycolic acid units, such as polylactic acid (PLA). The central member may also be constructed from high-tensile strength polymers, such as Tyvek™ (high-density polyethylene fibers) or Kevlar™ (para-aramid fibers). In an embodiment, central member is constructed from biodegradable suture, such as VICRYL™ (polyglactin 910) suture available from Ethicon Corp., Somerville, N.J.

In some embodiments the central member can be used to direct placement after the device 240 has self-assembled. In some embodiments, additional mechanical features can be bound between the magnetic segments 140 to minimize out-of-plane motion during delivery and deployment, in similar manner as described with respect to the exoskeleton 120.

Figure 17:
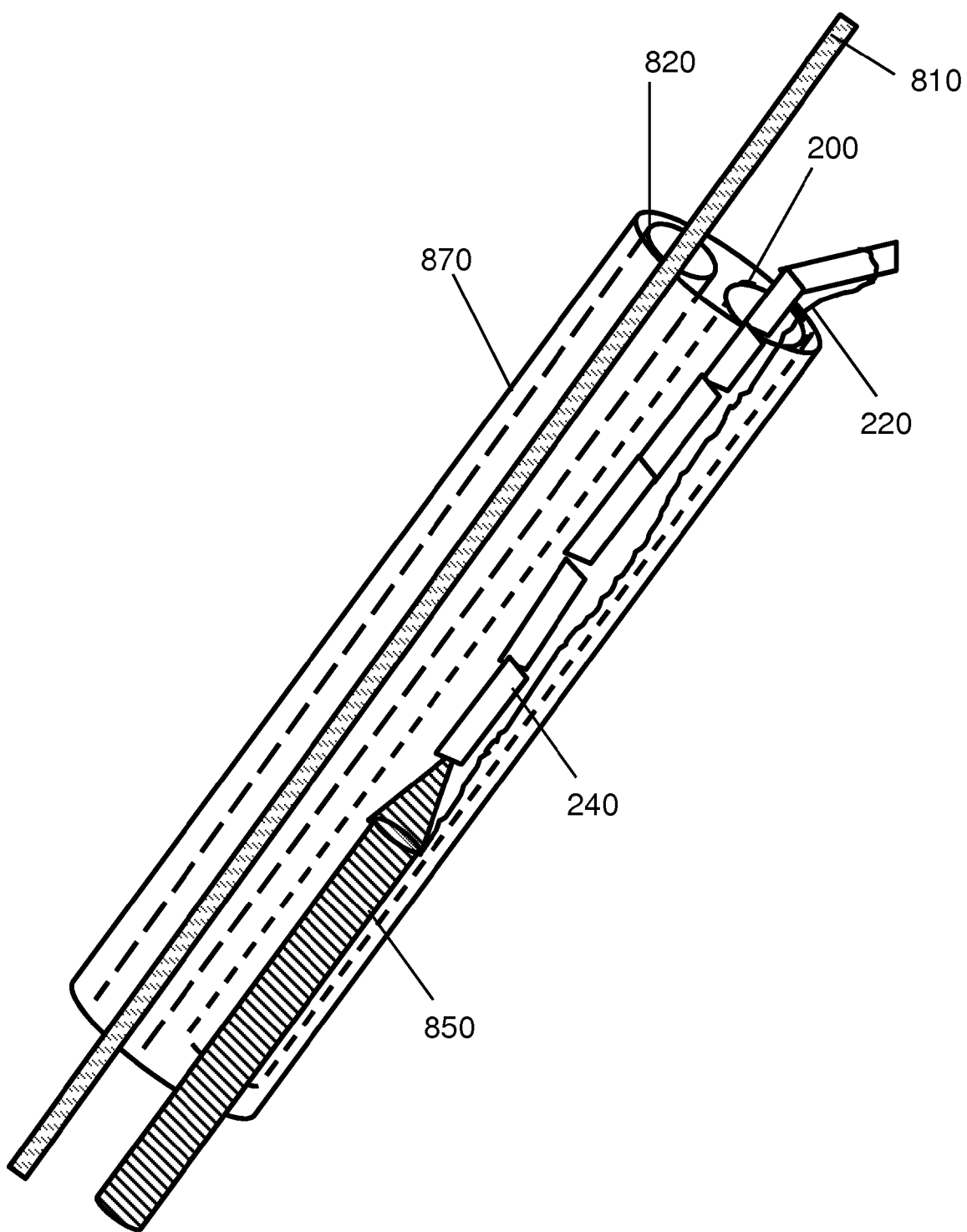
FIG. 17 is an alternative embodiment for delivering a self-assembling magnetic anastomosis device through a catheter with a pusher.

In other embodiments, the magnetic self-assembling anastomosis devices can be delivered with a simple delivery catheter, 870, as shown in FIG. 17. The delivery catheter 870 simply has a first lumen 200 for delivering the device 240 and a second lumen 820 for guiding the delivery catheter 870 to the location of the desired anastomosis. As shown in FIG. 17, the delivery catheter 870 rides along guide wire 810 to the delivery location. The second lumen 820, e.g., the guide lumen may run the length of the delivery catheter 870, or it may only run part of the length of the delivery catheter 870.

Other devices can also be used to replace the guide tube 550. For example, as shown in FIG. 17, flexible pusher 850 can be used to deliver the device 240 to the desired location of the anastomosis. As shown in FIG. 17, the device 240 may be coupled to a guide element 220, allowing the guide element 220 to be used to assemble the device 240 and to direct placement of the device 240. However, in some embodiments, there may not be a guide element 220. In other embodiments, the device 240 will include radial members 510 (not shown in FIG. 17) and the flexible pusher 850 may have an attachment point that allows the tip of the pusher to direct the center 530 to the desired location once the device 240 is deployed. The flexible pusher can be made from a semi flexible, biocompatible material, preferably non-magnetic, such as a biocompatible plastic, e.g., PTFE.

Figure 18D:
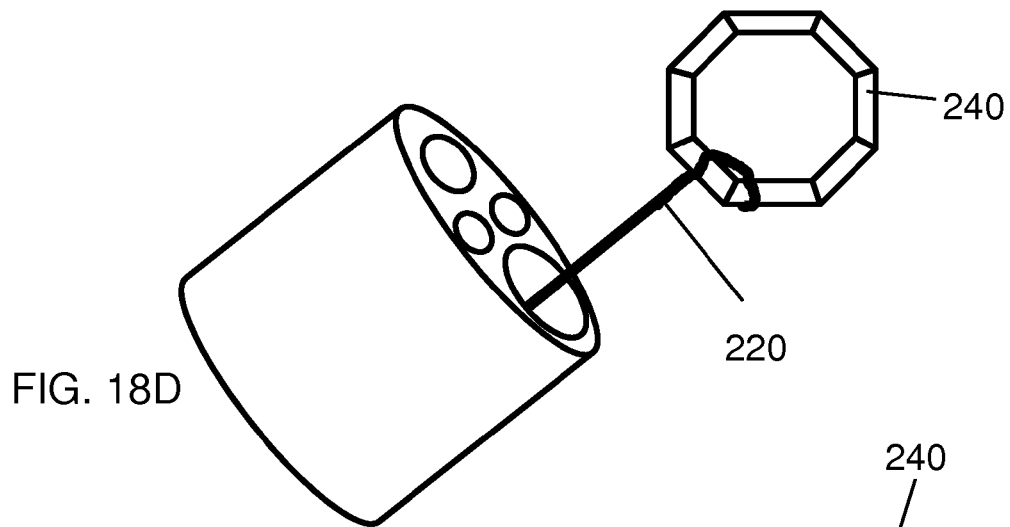
FIG. 18D depicts manipulation of an anastomosis device coupled to a guide element and a guide tube.
Figure 18E:
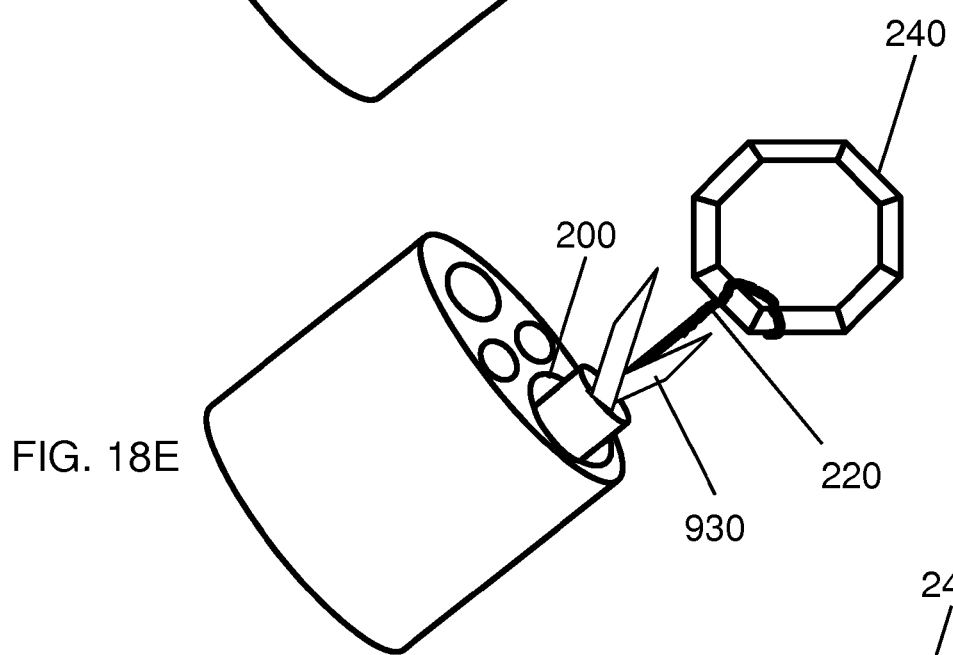
FIG. 18E depicts uncoupling an anastomosis device from a guide element and a guide tube.

The interaction between the guide tube 550, the guide element 220, and the device 240 is illustrated in greater detail in FIGS. 18A-18F. As shown in FIG. 18A, the device 240 is coupled to the guide element 220, which runs through a lumen of the guide tube 550. The device 240 in FIGS. 18A-18F is depicted as an octagon, as would be achieved with a self-assembling anastomosis device with eight magnetic segments; however, the device 240 could be any ring or polygon, self-assembling or otherwise. As shown in FIG. 18B, the guide tube 550 is delivered via a lumen 200, which can be the working channel of an endoscope. The guide tube 550 can also be delivered via a trocar, catheter, or fine needle aspiration device.

Figure 18F:
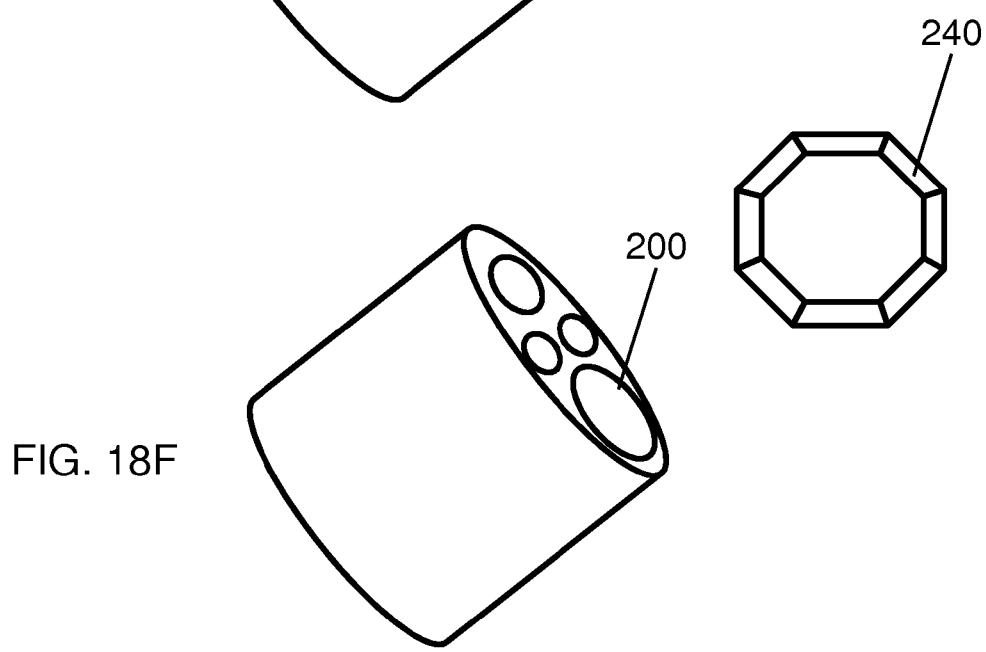
FIG. 18F depicts removing a delivery device from an anastomosis device.

After delivery, the device 240 can be brought into contact with the guide tube 550 by applying a proximal force to the guide element 220, as shown in FIG. 18B. Once the guide tube 550 contacts the device 240, it is possible to manipulate the device 240 by translating the guide tube 550, as shown in FIG. 18C, i.e., the "tight hold". In some embodiments, it is also possible to rotate the device 240 by rotating guide tube 550 (not shown). Accordingly, the guide tube 550 may be independently translatable and rotatable relative to the delivery device through which the guide tube 550 is received (e.g., working channel or lumen 200 of an endoscope, a trocar, cannula, catheter, or needle). Similarly, because the guide tube 550 is coupled to the device 240 by way of one or more guide elements 220, the device 240 can further be positioned or manipulated independently of the delivery device (e.g., endoscope, trocar, cannula, catheter, needle, etc.). Thus, the device 240 may be translatable and/or rotatable independent of the delivery or access device. Using the guide tube 550, the device 240 can be placed into a rough location, as which point the guide tube 550 is withdrawn from the device 240 while the guide element 220 remains coupled to the device 240, as shown in FIG. 18D. As discussed above, this "loose hold" configuration allows a user to manipulate the patient and the device 240 in order to achieve an optimum position, but with the guide tube 550 out of the way. Additionally, should it be needed, the guide tube 550 can be returned to the device 240, as in FIG. 1C, to allow further manipulation. Once the device 240 is in place, the guide element 220 can be uncoupled from the device 240, using, e.g., cutting element 930, as shown in FIG. 18B. The cutting element 930 is depicted as a scissors-type instrument, however, any cutting tool such as a sharp edge or a cautery wire will also work. Once the device 240 has been uncoupled from the guide element 220, the delivery instrument can be removed from the device 240, as shown in FIG. 18F.

Figure 19:
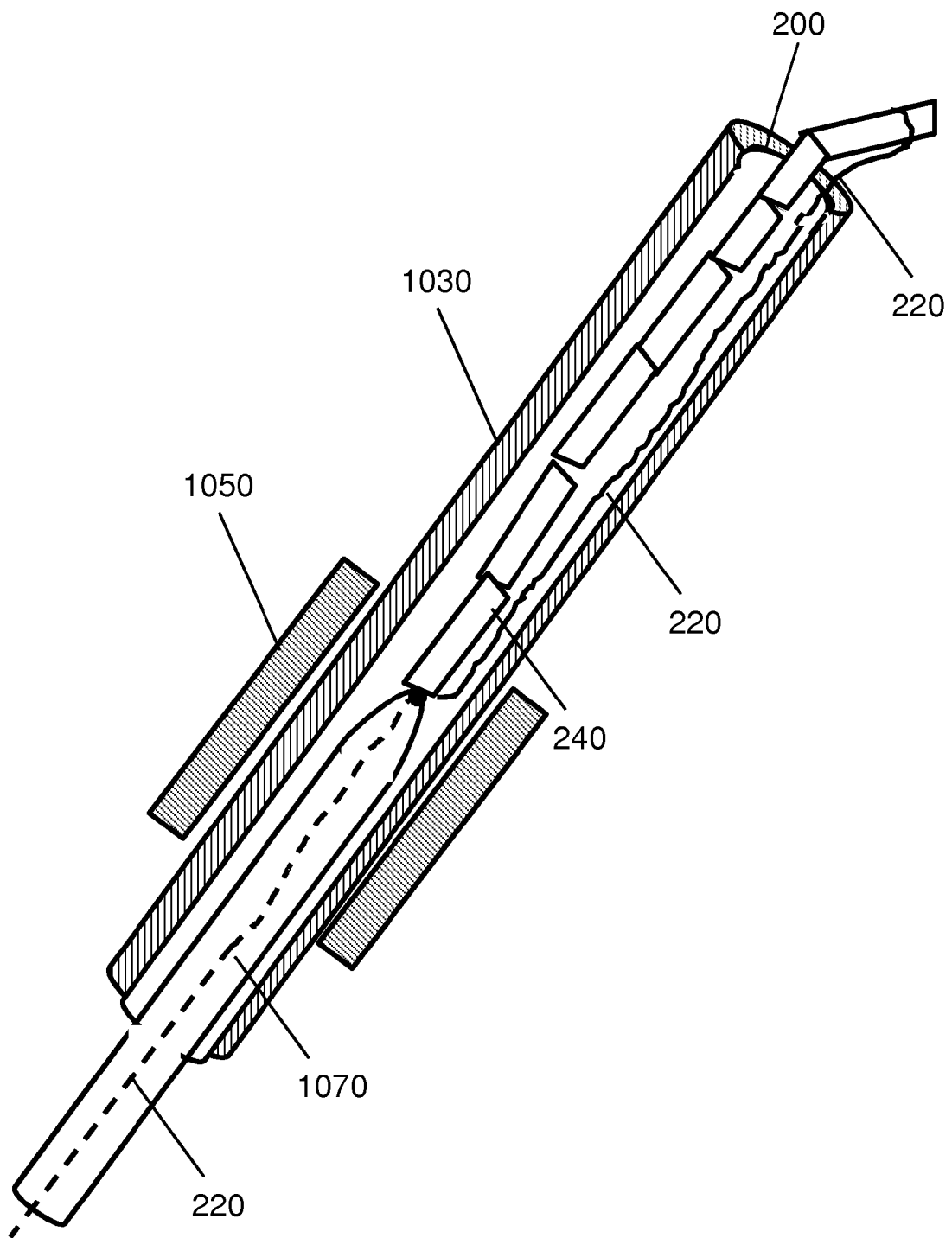
FIG. 19 illustrates delivery of a self-assembling magnetic anastomosis device through a trocar with the use of an elongated manipulator.

In another embodiment, a device 240 can be delivered to a tissue with a system including a delivery catheter 1030 which is placed through a trocar 1050, such as used in a laparoscopic procedure. As shown in FIG. 19, a self-assembling device 240 with a guide element 220 attached thereto can be pushed through a delivery catheter 1030 with an elongated manipulator 1070 having a lumen through which the guide element 220 can be run. Similar to FIGS. 2-5 and 9-15, above, the guide element 220 may have one or multiple connection points with the device 240, or the device may include radial elements 510 (not shown in FIG. 19). Additionally, as described above with respect to the guide tube 550 delivery, the elongated manipulator 1070 also provides the flexibility of both "tight hold" and "loose hold" by bringing the elongated manipulator 1070 to the device 240 and then retracting the elongated manipulator 1070 from the device 240 while the device 240 remains coupled to the guide element 220.

Figure 20A:
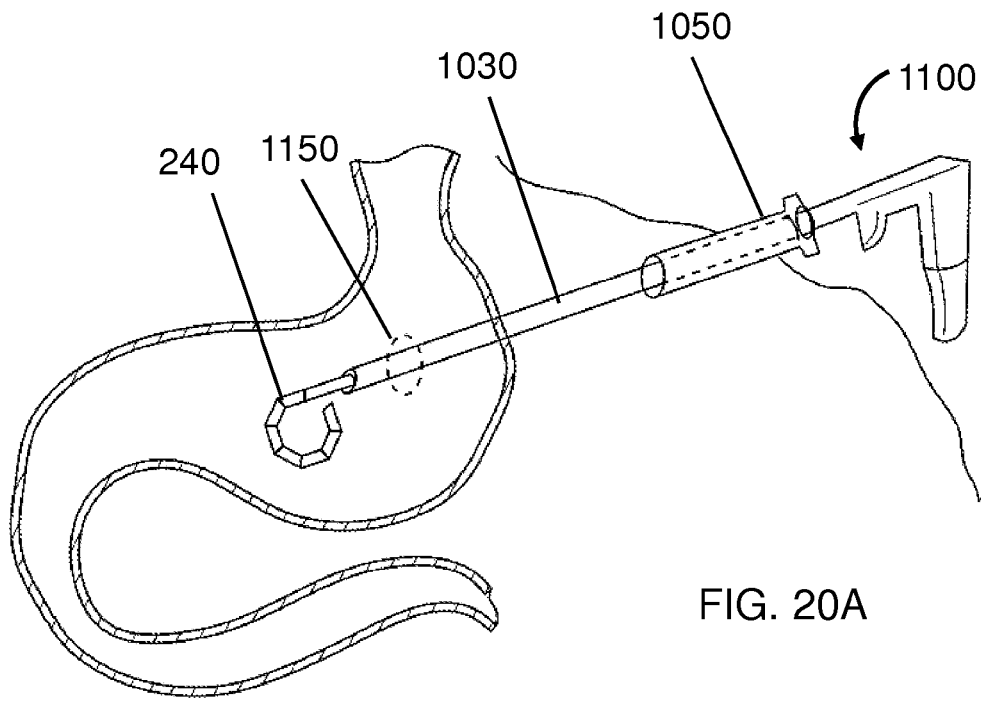
FIG. 20A depicts delivering a self-assembling magnetic anastomosis device laparoscopically.

Using a trocar 1050, it is simple and quick to deliver a device 240 to a variety of anatomical targets. As shown in FIG. 20A, it is merely a matter of entering the body with a trocar 1050 (or providing another port), at which point a delivery catheter 1030 is brought to (or through) a tissue, wherein the device 240 can be deployed with the elongated manipulator 1070 (not shown in FIG. 20A or 20B). The elongated manipulator 1070 may be constructed from rigid metal or a polymer, allowing the elongated manipulator 1070 to be manipulated through the trocar 1050 and the delivery catheter 1030. Typically, the delivery will be visualized with a laparoscope (not shown) brought to the surgical field through a separate trocar or port.

Figure 20B:
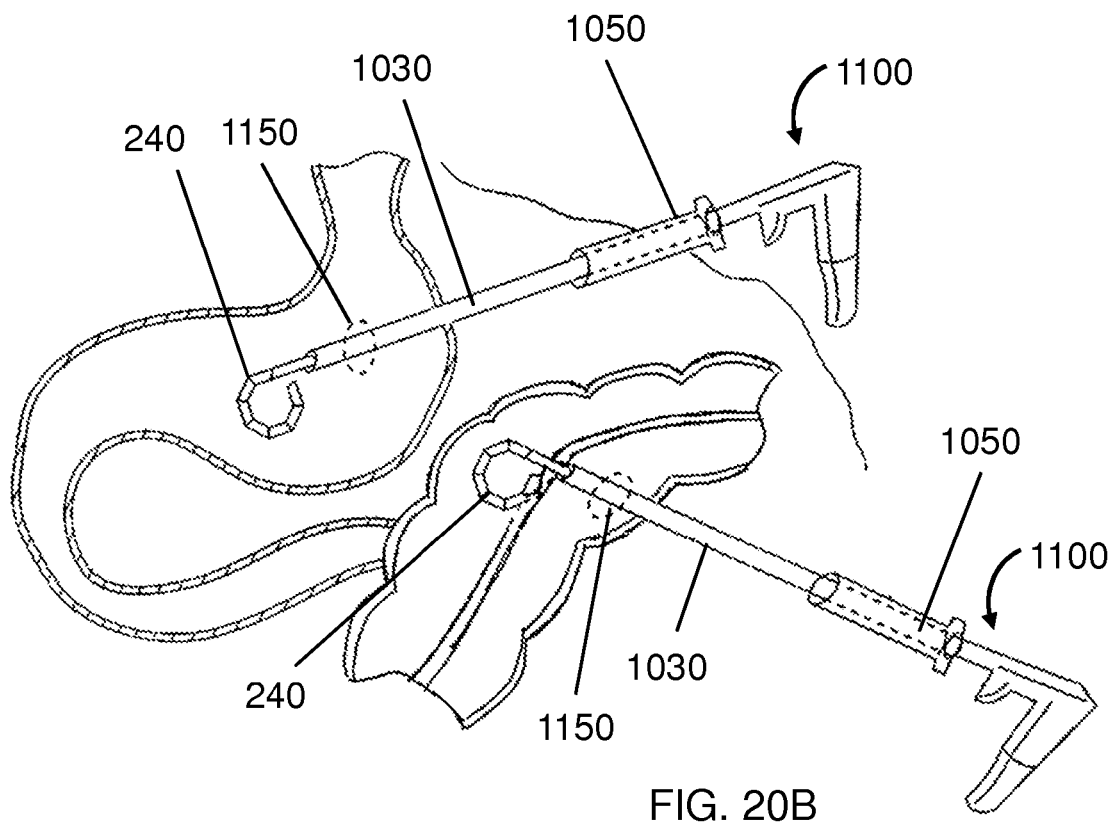
FIG. 20B depicts delivering self-assembling magnetic anastomosis devices laparoscopically.

In some embodiments, such as shown in FIG. 20B, two separate laparascopic delivery devices 1100 can be used to deploy mating devices 240 in order to form an anastomosis. In other embodiments, a single laparoscopic delivery device 1100 can be used to deliver a first device 240 and a second device can be delivered with another delivery method, such as with an endoscope, e.g., as discussed above and shown in FIGS. 18A-18F. In other embodiments, a first device 240 can be delivered with a laparoscopic delivery device 1100, and the laparoscopic delivery device 1100 subsequently removed and reloaded with a second device 240 for mating with the first device.

Figure 21:
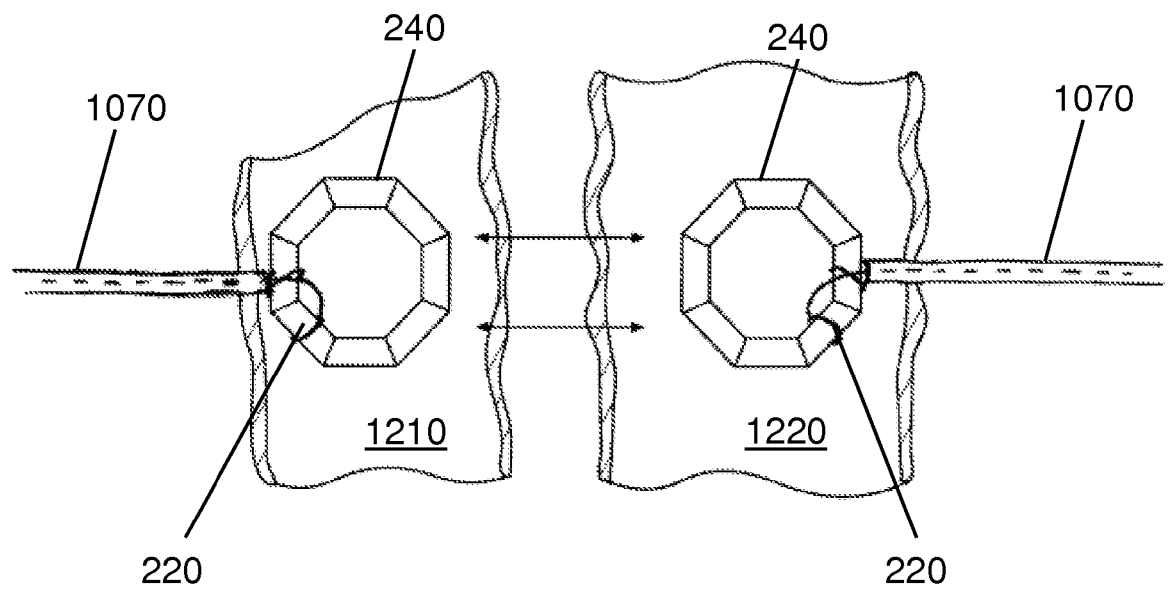
FIG. 21 depicts coupling first and second magnetic anastomosis devices coupled to first and second guide elements.
Figure 21:
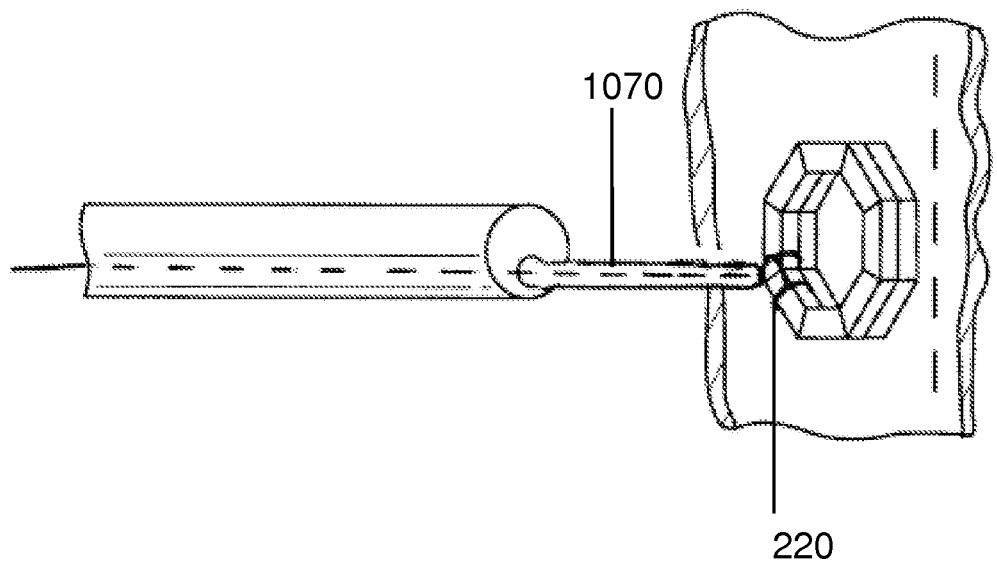
Figure 22:
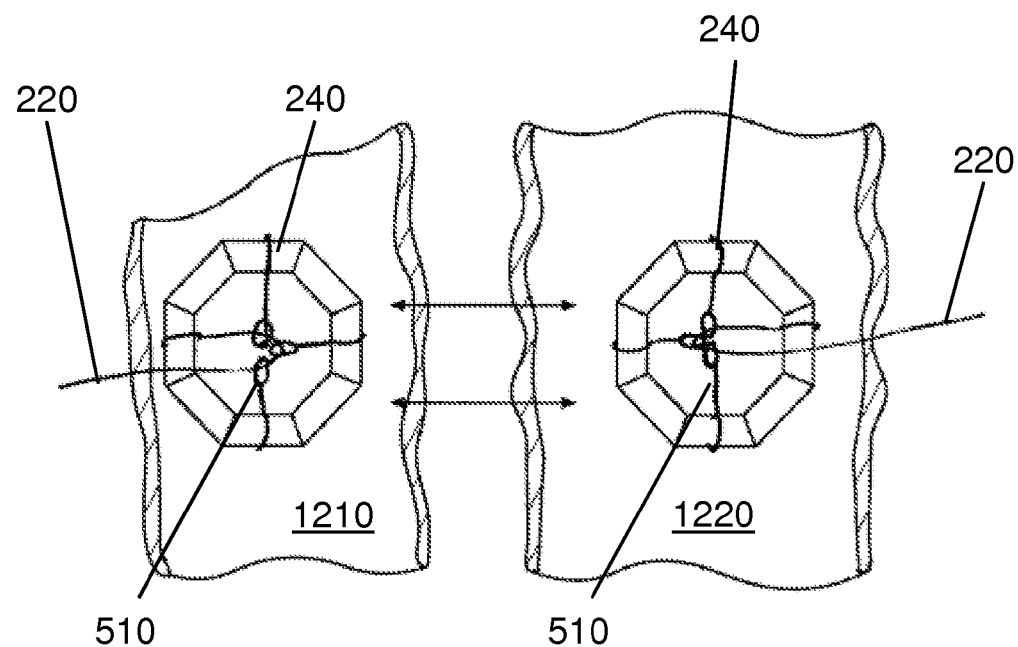
FIG. 22 depicts coupling first and second magnetic anastomosis devices coupled to first and second guide elements.
Figure 22:
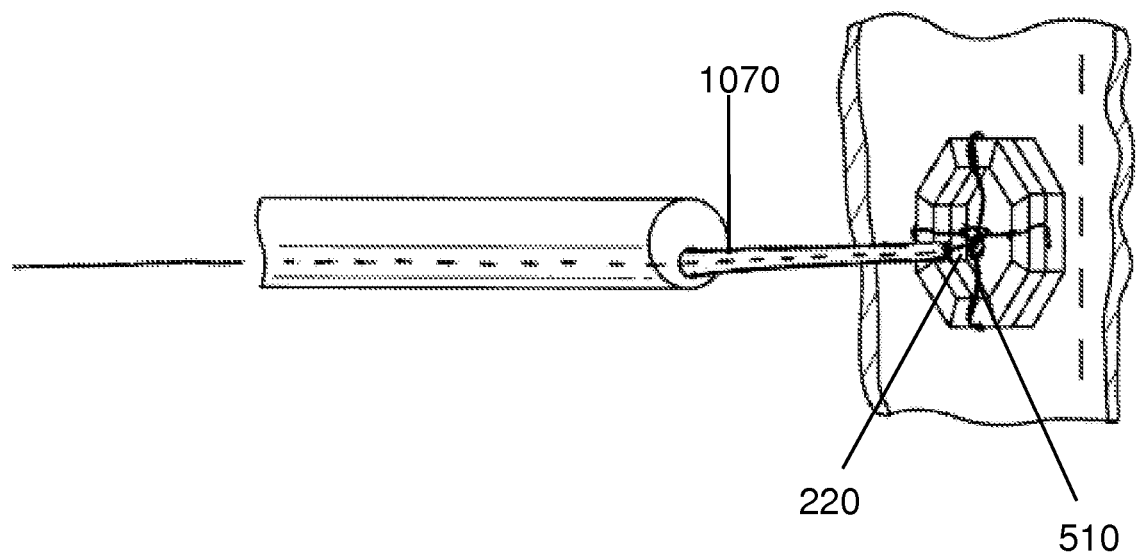

Mating of first and second devices 240 is shown in greater detail in FIGS. 21-26. The mating works similarly regardless of the delivery method, e.g., with an endoscope, a delivery catheter, a trocar 1050, or via another port. As shown in FIG. 21 two devices 240, each coupled to a guide element 220 are brought to opposite sides of tissues 1210 and 1220, through which an anastomosis is to be formed. Once the two devices 240 are brought into proximity, the devices 240 mate and bring the tissues 1210 and 1220 together. With time, an anastomosis of the size and shape of the devices 240 will form and the devices will fall away from the tissue. A similar technique is used when devices comprising radial members 510 are used to create an anastomosis, e.g., as shown in FIG. 22. While FIGS. 21 and 22 depict manipulation of the devices 240 with an elongated manipulator 1070, one or both of the devices 240 can be delivered with a guide tube 550, as described above. Additionally, while the devices 240 are shown being positioned with the elongated manipulator 1070 tight against the device, it is understood that it may be beneficial to use a "loose hold" configuration to allow the devices 240 to mate without the interference of the elongated manipulators 1070. It is to be understood that multiple combinations of magnetic anastomosis delivery methods (e.g., endoscope, delivery catheter, laparoscope) can be used.

Another benefit of the disclosed magnetic anastomosis systems is that the mated devices 240 create enough compressive force to quickly stop the blood flow to the tissues trapped between the devices 240. As shown in FIGS. 20A and 20B, a surgeon may quickly access the interior of an organ (e.g., stomach, small intestine, bowel) but making an incision 1150 into the organ and then delivering the device 240 through the incision 1150, and then deploying the device 240 so that the device 240 circumscribes the incision. Once the mating device 240 is delivered, the blood flow to the incision is quickly cut off. Thus, a surgeon does not need to close the incision 1150 in the organ, speeding the procedure and requiring few instruments (e.g., laparoscopic stapler). The technique of circumscribing an incision 1150 with the device 240 can be done for both devices 240, or one device 240 can be delivered, e.g., with an endoscope, and the second device 240 delivered through an incision 1150.

In some embodiments, the two mating magnetic anastomosis devices can be visualized directly, e.g., using an endoscopic or laparoscopic camera. In other instances, the two mating magnetic anastomosis devices can be monitored with ultrasound or another medical imaging technique, such as fluoroscopy. In some embodiments, the visualization will be provided with the delivery device. In some embodiments, the visualization will be achieved with a separate device. Other techniques, known in the art, such as dyes, contrast, and gas delivery may also be used to assist visualization of the mating devices.

Figure 23A:
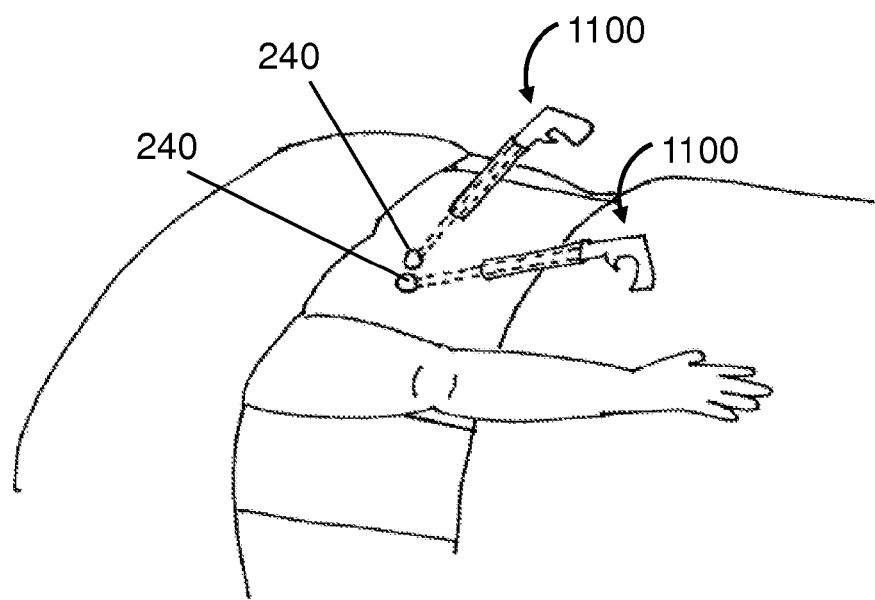
FIG. 23A depicts deploying first and second magnetic anastomosis devices to a patient in a first position.
Figure 23B:
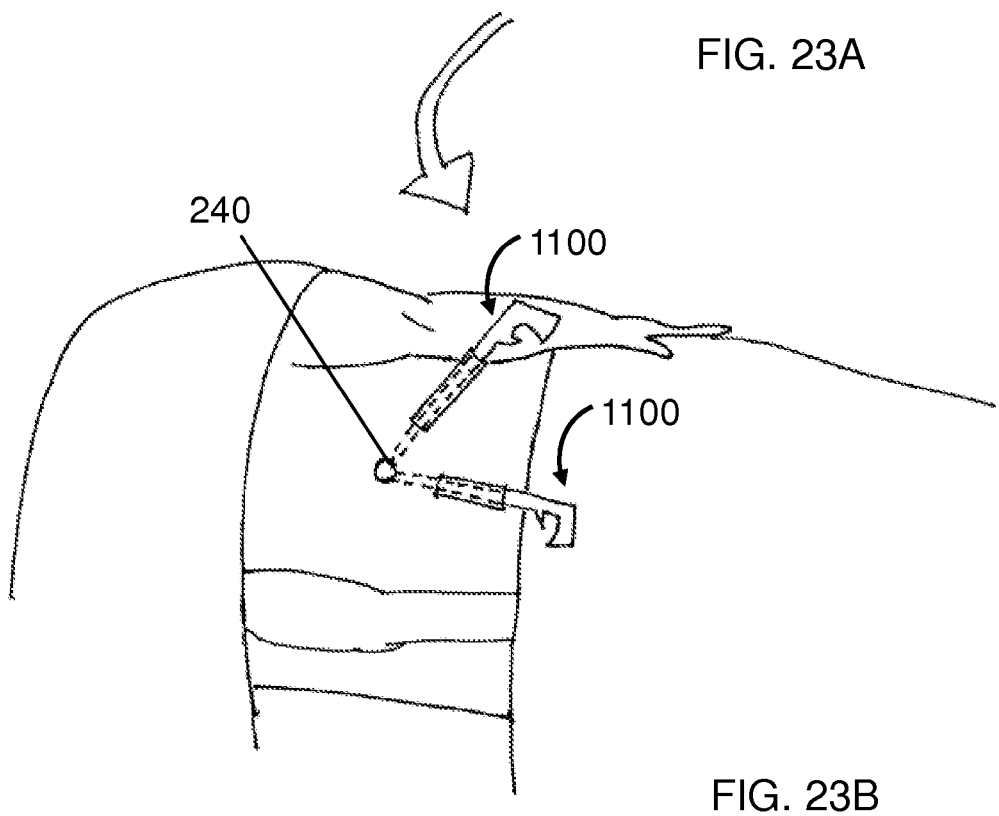
FIG. 23B depicts deploying first and second magnetic anastomosis devices to a patient in a second position.

In addition to manipulating the device 240 with the guide tube 550 or an elongated manipulator 1070, it may be beneficial in some instances to actively manipulate the body of the patient during the procedure, as shown in FIGS. 23A and 23B. FIG. 23A may be, for example, a procedure where two laparoscopic delivery devices 1100 are used to deliver two devices 240 to two tissues to be joined, e.g., as shown in FIG. 20B. While it may be easier to visualize the tissues when the patient is on his or her back, as shown in FIG. 23A, it may be easier to join the two tissues by manipulating the patient, as shown in FIG. 23B, so that the tissues are in closer proximity or otherwise in a superior alignment for the devices 240. In some instances, it may also be beneficial to add addition mass to the device 240 or the tissue to improve the alignment of the devices 240, with or without manipulation of the patient, as discussed in greater detail below. During patient manipulation, it is often beneficial to retract the elongated manipulators 1070 from the devices 240, i.e., to assume the "loose hold" position, so that the magnetic devices can find their lowest energy configuration. Because the devices 240 are still coupled to the guide elements 220, however, it is quite easy to reposition one or both devices 240 as needed.

Figure 24A:
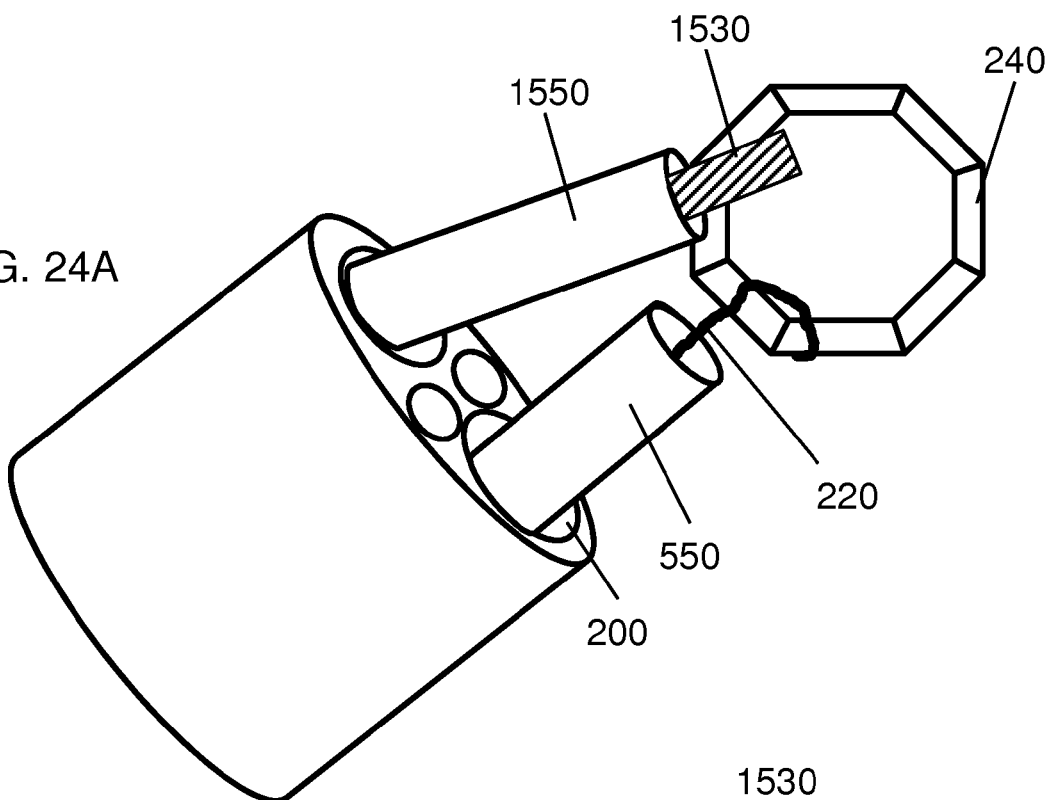
FIG. 24A depicts delivering a removable weight to a magnetic anastomosis device via an auxiliary catheter.
Figure 24B:
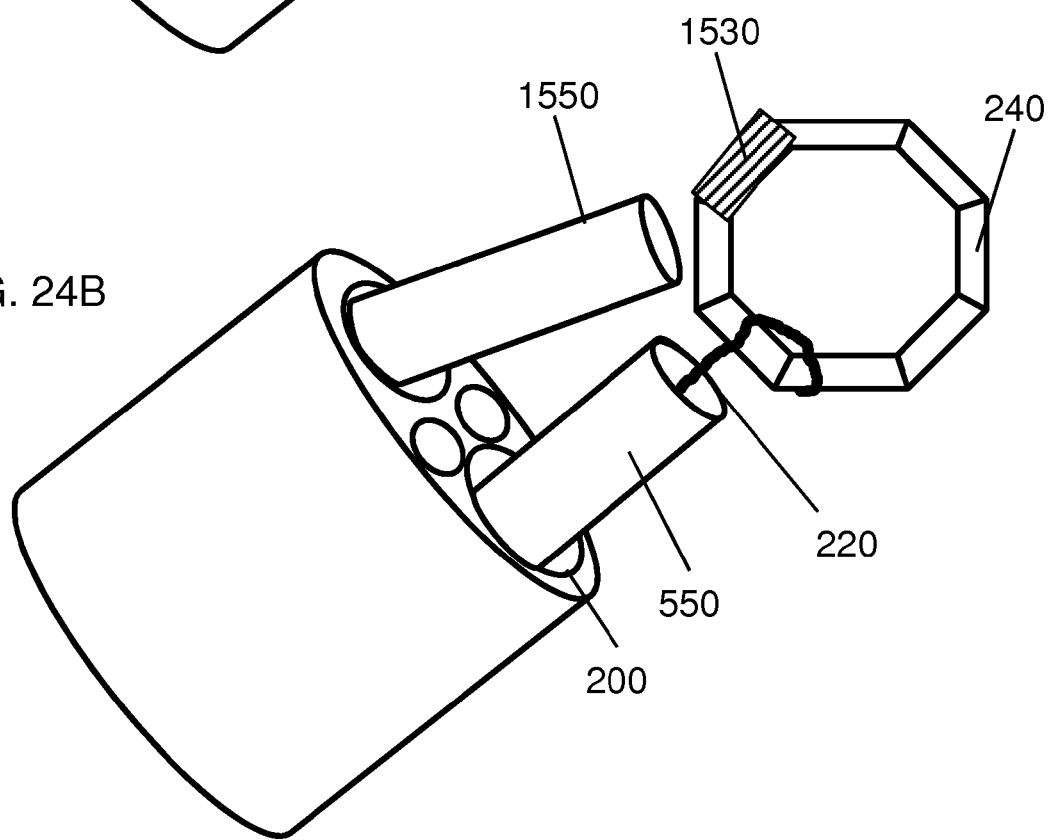
FIG. 24B depicts retracting an auxiliary catheter from a magnetic anastomosis device after delivering a removable weight.
Figure 24C:
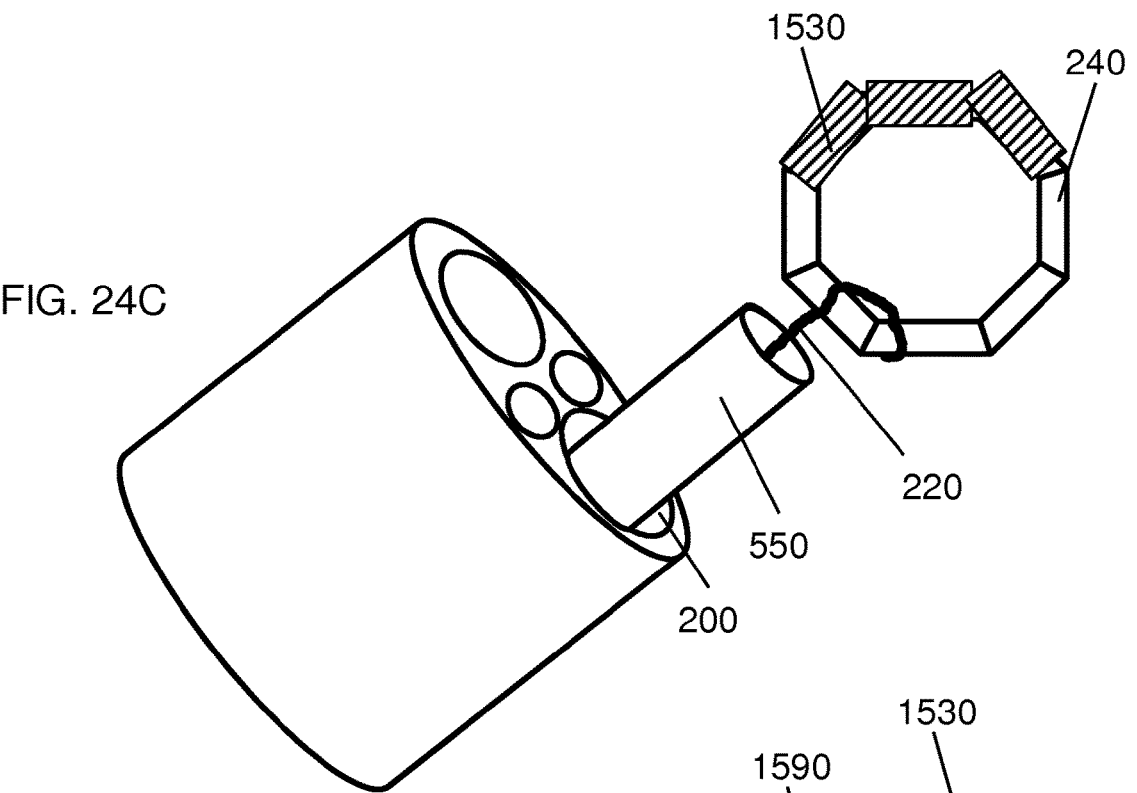
FIG. 24C depicts manipulating a magnetic anastomosis device with removable weights attached thereto.
Figure 24D:
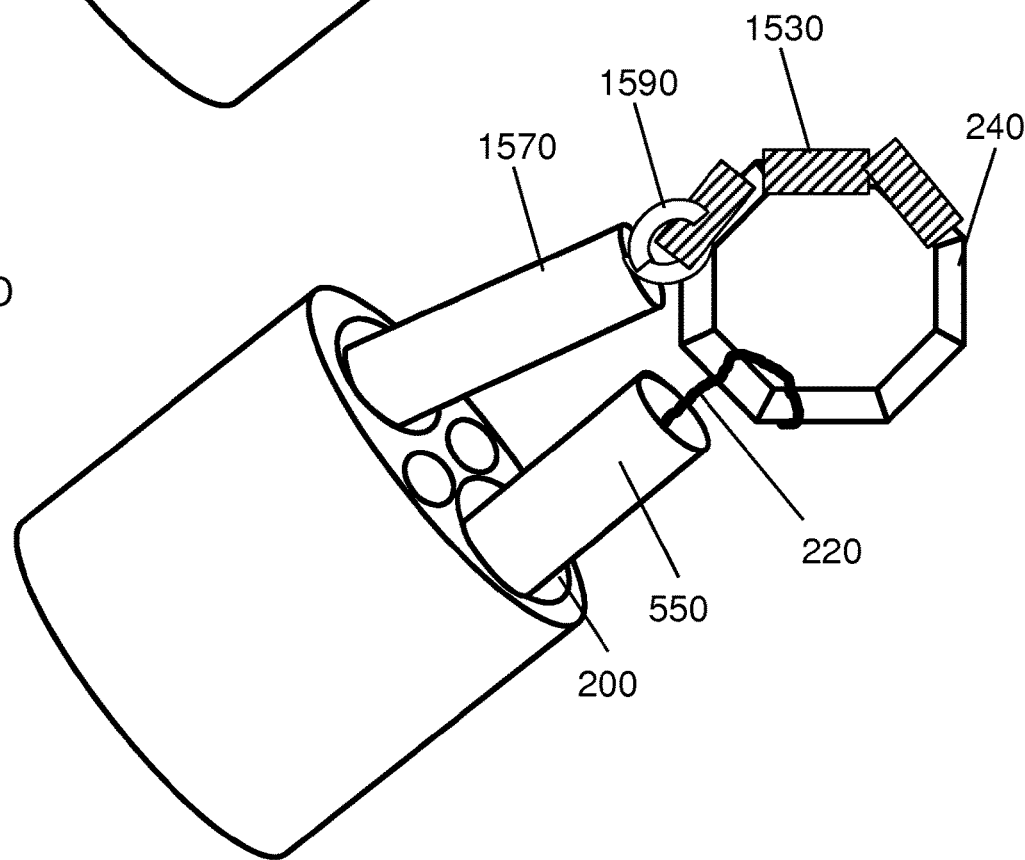
FIG. 24D depicts removing removable weights from a magnetic anastomosis device with an auxiliary manipulator.

One method for changing the weight (adding mass) to a magnetic anastomosis device is depicted in FIGS. 24A-24D. Using a configuration similar to that shown in FIG. 18A-18F, a device 240 coupled to a guide element 220 is delivered to a tissue using a guide tube 550 delivered through a lumen 200 (e.g., a working channel of an endoscope). Once the device 240 is in approximate position, an auxiliary catheter 1550 is brought to the device 240 enabling removable weights 1530 to be attached to the device. In some embodiments the removable weights 1530 are ferromagnetic, so they are naturally attracted to the magnetic segments 140 in the device. Such removable weights 1530 may be coated to improve the biocompatibility, e.g., by coating the removable weights with a polymer, such as PTFE. In alternative embodiments, the removable weights 1530 may be coupled to the device 240 with a biocompatible adhesive or gel. Once the removable weights 1530 are delivered to the device 240, the auxiliary catheter 1550 is retracted from the device, as shown in FIG. 24B. The final device 240 with removable weights 1530 may appear as shown in FIG. 24C. The additional weight provided to the device 240 will make it easier to manipulate the device 240 and assist the device in meeting a mating device on an adjacent tissue. As shown in FIG. 24C, the guide element 220 and/or the guide tube 550 can be used to manipulate and place the weighted device 240. In addition, the patient may be moved to help the weighted device 240 mate with another device, as described above with respect to FIGS. 23A and 23B. Finally, once the device 240 has achieved the proper position, the removable weights 1530 can be removed from the device 240 with an auxiliary manipulator 1570, to assure that the mated devices do not move from their final positions due to the excess weight.

Methods for adding additional weight to devices 240 of the invention are not limited to the embodiment shown in FIG. 24A-24D, however. For example, the removable weights can be delivered through a trocar or other port to achieve the functionality described above. In alternative embodiments, a balloon catheter (not shown) can be delivered to the device 240 or nearby the device 240 and then filled with fluid to facilitate movement of the device 240. Such techniques are especially useful in positioning a device 240 that is located within a lumen that can be easily accessed and filled using a balloon catheter, such as the small intestine.

Figure 25:
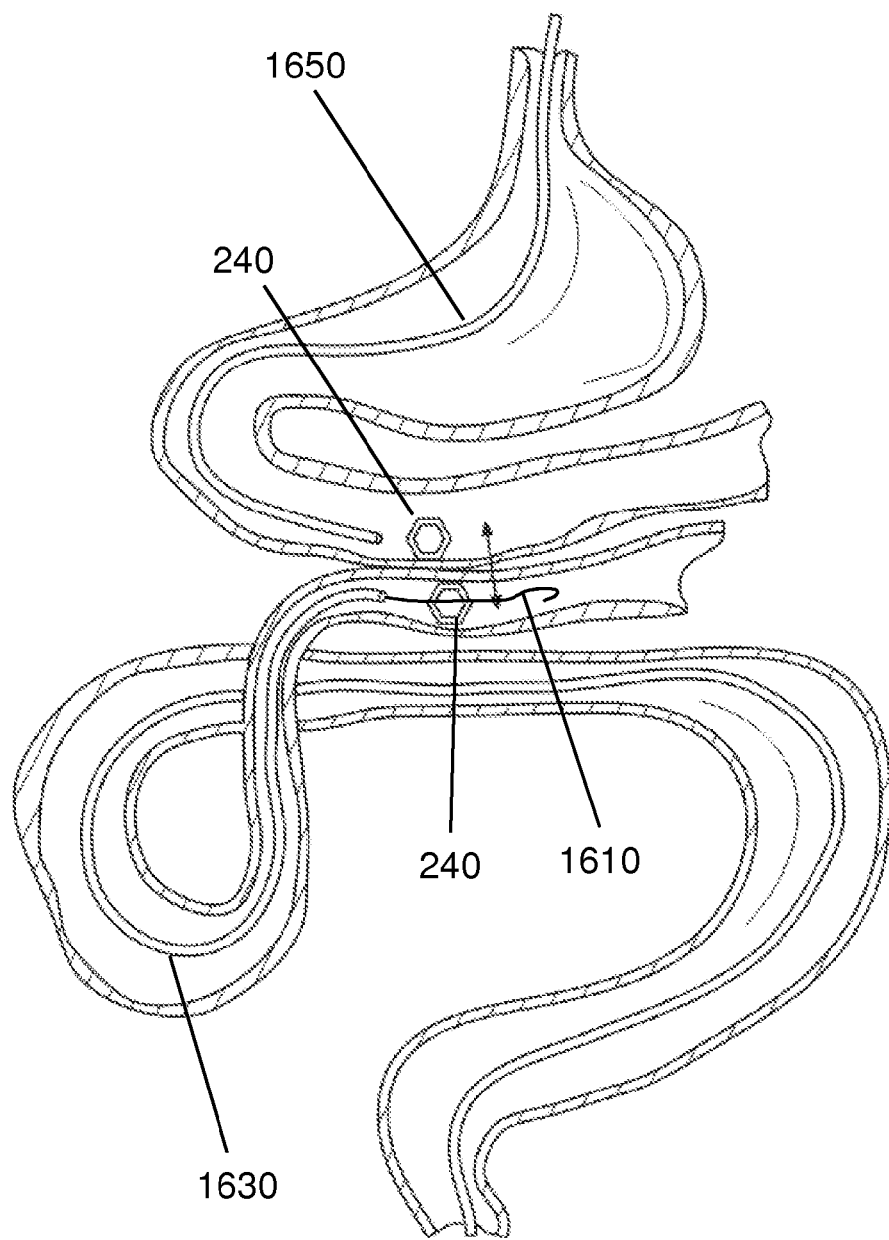
FIG. 25 depicts the creation of an anastomosis between organs of the gastrointestinal tract with by delivering a first magnetic anastomosis device with an endoscope and a second magnetic anastomosis device with a delivery catheter.

The devices and methods described above need not be used in isolation. For example, as shown in FIG. 25, a first device 240 may delivered with an endoscope 1650 and a second device 240 delivered with a delivery catheter 1630 that is directed to the anastomosis via guide wire 1610. In some embodiments, the guide wire 1610 may be delivered to the site of the anastomosis independently, and in other embodiments, the guide wire 1610 may be deployed using the same tool that delivered the first device 240. For example, a first device 240 may be deployed and an incision made through the annular middle of the device and the guide wire 1610 deployed there through so that the delivery catheter 1630 necessarily is directed to the location of the first device 240.

Figure 26:
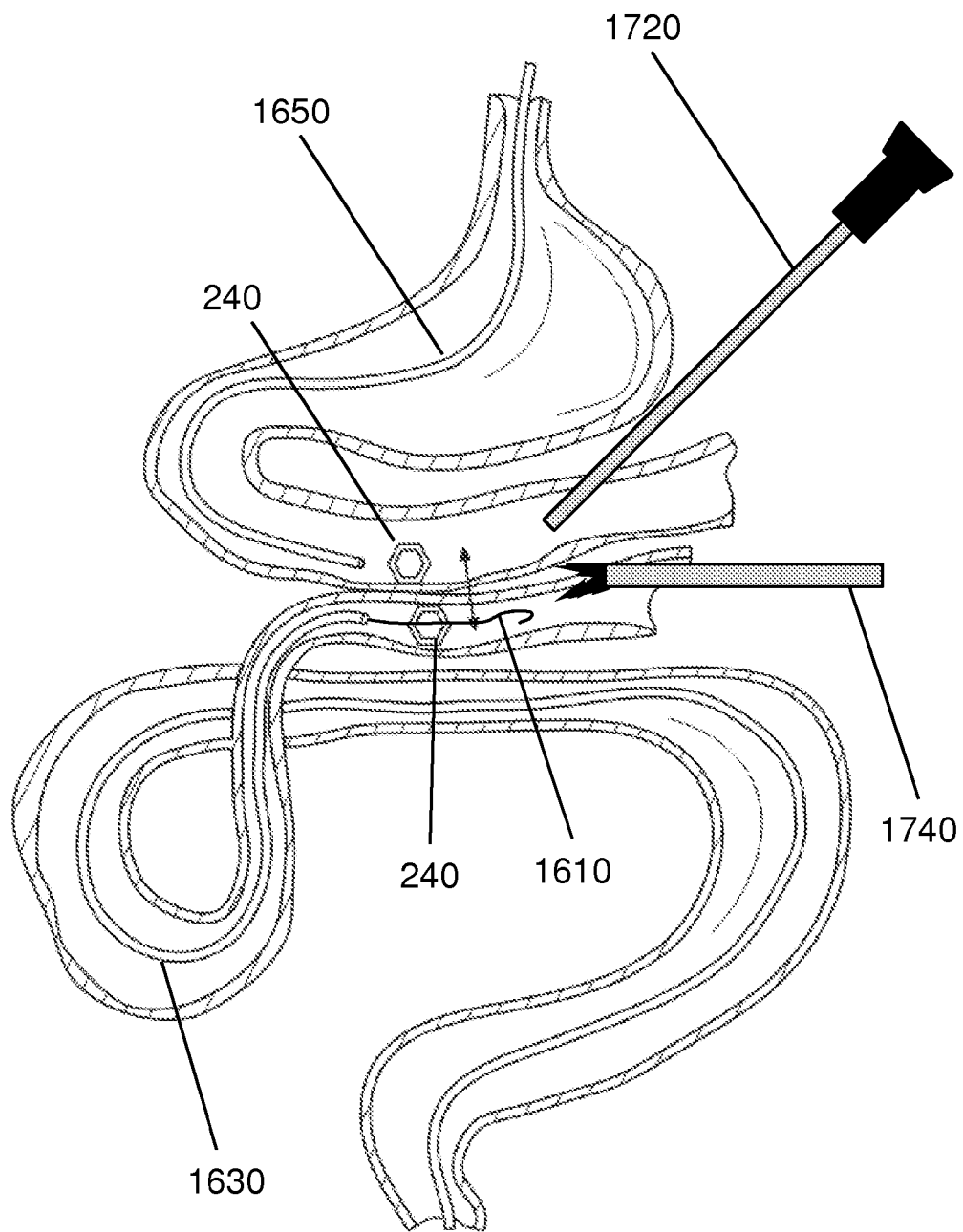
FIG. 26 depicts guiding two mating magnetic anastomosis devices together with laparoscopy.

Devices to be joined may also be guided into alignment with independent surgical manipulation, e.g., laparoscopic assistance, as shown in FIG. 26. The manipulation may be of the devices 240, or of the organ, or both. For example, in the embodiment shown in FIG. 26, first and second device 240 are delivered with an endoscope 1650 and a delivery catheter 1630 respectively. Because the devices 240 are visible through the tissue using a laparoscope 1720, it is straightforward to manipulate the bowel with a laparoscopic grasper 1740 to bring the two segments together, e.g., by grabbing a loop of bowel having the first device 240 and bringing it into alignment with a second device 240.

Figure 27:
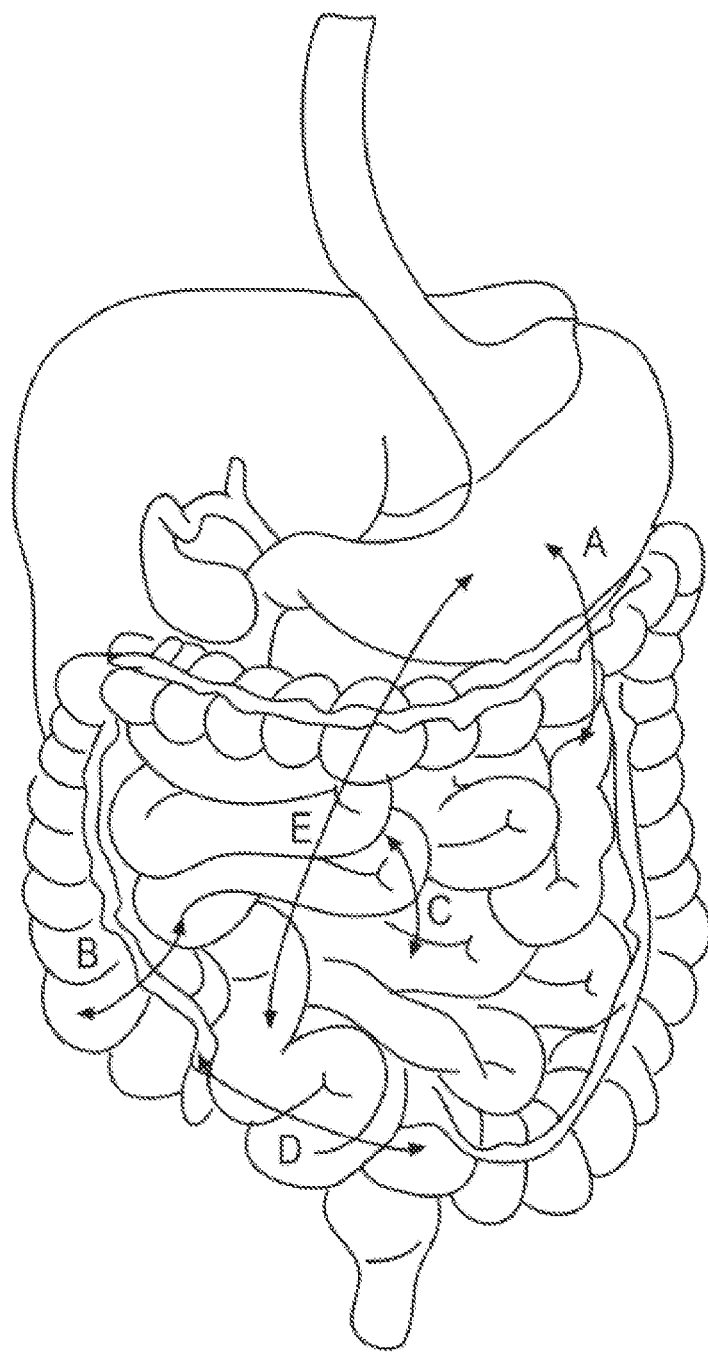
FIG. 27 depicts the creation of an anastomosis between organs of the gastrointestinal tract.
Figure 28:
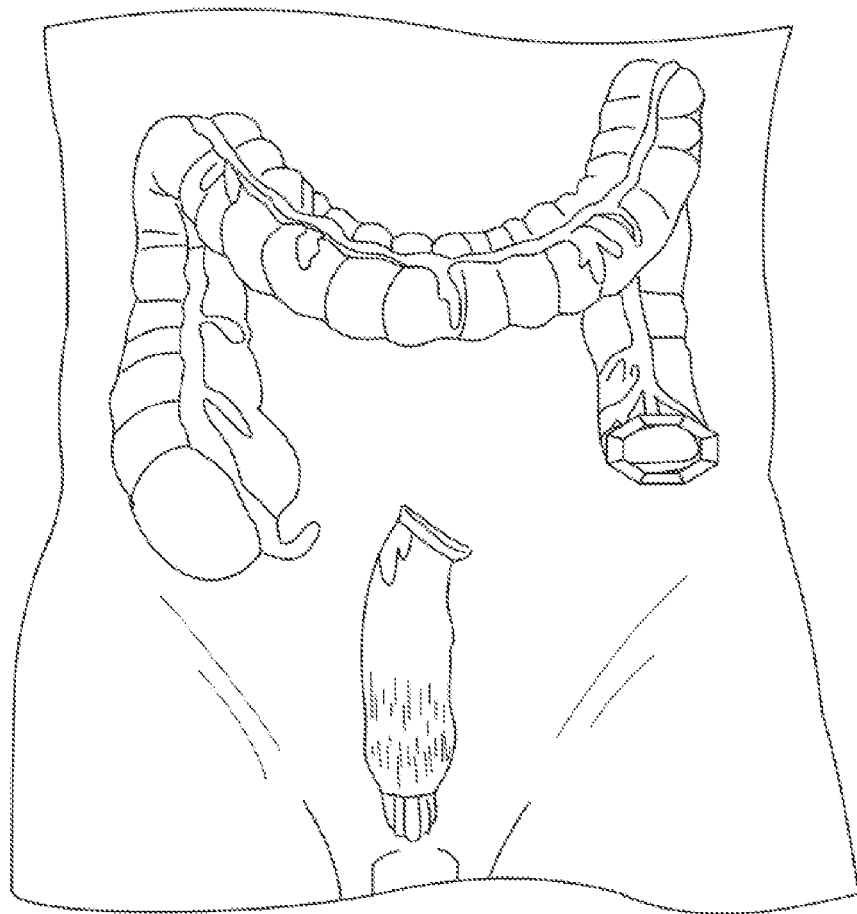
FIG. 28 depicts joining two sections of colon with magnetic anastomosis devices after a section of the colon has been removed.

Thus, using the devices and methods of the invention, it is possible to create anastomoses between tissues and organs in the gastrointestinal tract. Using endoscopic techniques and laparoscopic techniques, the devices of the invention allow for the creation of a variety of anastomoses between the various organs of the gastrointestinal tract, such as the stomach, small intestine, gall bladder, and colon, as shown in FIG. 27. Such techniques can be used for management of disease, such as obesity and diabetes, or such techniques can be used to improve function in the wake of disease, such as cancer. Such techniques can also be used for repair, for example, to connect portions of healthy colon after a portion of diseased colon has been removed, as shown in FIG. 28.

The devices, systems, and methods described herein am directed to forming an anastomosis between adjacent tissues or organs. In particular embodiments, the tissues are adjacent gastrointestinal organs, such as, for example, the stomach and the gallbladder, the small intestine and the gallbladder, the stomach and the duodenum, or the ileum and the colon. When deployed in adjacent tissues, for example adjacent organs or different regions of the same organ, pairs of coupled magnetic devices create a compressive ring that can be surgically opened, or allowed to form an anastomosis without further intervention. When paired devices are left alone, the compressive force against the tissues collapse the vasculature and extrude fluids in the tissues, further reducing the distance between the devices and increasing the magnetic attraction. With time, the coupled devices eventually couple completely and fall away, leaving a formed anastomosis.

It should be noted that in some applications, pairs of magnetic devices can be used to create vascular anastomoses or to treat cardiac conditions. For example, a magnetic anastomosis coupling can be formed between adjacent blood vessels with magnetic devices. For example, a pair of magnetic devices can be delivered with a vascular delivery device, such as a catheter.

INCORPORATING BY REFERENCE

References and citations to other documents, such as patents, patent applications, patent publications, journals, books, papers, web contents, have bean made throughout this disclosure. All such documents are hereby incorporated herein by reference in their entirety for all purposes.

EQUIVALENTS

The invention may be embodied in other specific forms without departing from the spirit or essential characteristics thereof. The foregoing embodiments are therefore to be considered in all respects illustrative rather than limiting on the invention described herein. Scope of the invention is thus indicated by the appended claims rather than by the foregoing description, and all changes which come within the meaning and range of equivalency of the claims are therefore intended to be embraced therein.

What is claimed is:

1. A method of forming an anastomosis comprising:
   providing a system comprising:
   a magnetic compression anastomosis device comprising a plurality of magnetic segments that self-assemble from an unassembled state into an assembled state having a geometric shape including a polygon or ring and a plurality of individual guide elements, each of the plurality of guide elements having a distal end directly coupled to a respective one of a set of the plurality of magnetic segments;
   an access device configured to provide access to an anatomical structure within a subject, the access device including an elongate manipulator within the access device and being independently translatable and rotatable relative to the access device, the elongate manipulator couplable to at least one of the plurality of guide elements; and
   a tension device separate from the magnetic compression anastomosis device and comprising a plurality of control members configured to independently receive input from a user, wherein each of the plurality of control members is directly coupled to a proximal end of a respective one of the plurality of guide elements and is configured to separately control an amount of tension applied to the respective guide element coupled thereto based upon direct user input with the control member;
   operating at least one of the plurality of control members to manipulate the magnetic compression anastomosis device in at least one of the unassembled state or the assembled state; and
   operating the elongate manipulator to direct placement of the magnetic compression anastomosis device relative to the anatomical structure within the subject, wherein the elongate manipulator is coupled to the at least one of the plurality of guide elements.

2. The method of claim 1, wherein the plurality of magnetic segments are coupled end-to-end to define a linear assembly having first and second ends, and the linear assembly forms the polygon or ring by spontaneously joining the first and second ends.

3. The method of claim 1, wherein the plurality of magnetic segments are coupled end-to-end to define the polygon or ring, and the polygon or ring is collapsible to form a linear assembly having a length of approximately one half the perimeter of the polygon or ring.

4. The method of claim 1, wherein the plurality of magnetic segments are coupled together with an exoskeleton that directs the self-assembly.

5. The method of claim 1, wherein the elongate manipulator comprises a lumen having a distal and proximal end and the at least one guide element is disposed within the lumen and is translatable from a distal to a proximal position.

6. The method of claim 1, wherein, upon assembly of the plurality of magnetic segments into the geometric shape, the distal ends of the plurality of guide elements are equidistantly spaced apart from one another.

7. The method of claim 1, wherein operating at least one of the plurality of control members comprises coordinating self-assembly of the plurality of magnetic members into the geometric shape.

8. The method of claim 1, wherein the access device houses a portion of each of the plurality of guide elements and is disposed between the magnetic compression anastomosis device and the tension device, and wherein the method further comprises inserting a portion of the access device into the body of the subject.

9. The method of claim 1, wherein the access device is selected from the group consisting of an endoscope, a laparoscope, a trocar, a cannula, a catheter, and a needle.

10. The method of claim 1, wherein the tension device comprises, for each of the plurality of control members, an independent locking mechanism for selectively and independently locking or unlocking the control member, and wherein the method further comprises operating the locking mechanism for one of the plurality of control members to lock said one of the plurality of control members to maintain tension between said one of the plurality of control members and the respective guide element coupled thereto.

11. The method of claim 1, wherein the tension device comprises, for each of the plurality of control members, an independent locking mechanism for selectively and independently locking or unlocking the control member, and wherein the method further comprises operating the locking mechanism for one of the plurality of control members to unlock said one of the plurality of control members to release tension between said one of the plurality of control members and the respective guide element coupled thereto.

12. The method of claim 1, wherein operating at least one of the plurality of control members comprises promoting disassembly of the geometric shape.

13. The method of claim 1, wherein operating at least one of the plurality of control members comprises altering the geometric shape.

14. The method of claim 1, wherein operating at least one of the plurality of control members comprises positioning the magnetic compression anastomosis device adjacent to tissue in the body of the subject.

15. The method of claim 1, wherein operating at least one of the plurality of control members comprises pairing the magnetic compression anastomosis device with a second magnetic compression anastomosis device in the body of the subject.

* * * * *